(12) United States Patent
Srivastava

(10) Patent No.: US 9,510,773 B2
(45) Date of Patent: Dec. 6, 2016

(54) MULTI-ELECTRODE APPOSITION JUDGMENT USING PRESSURE ELEMENTS

(71) Applicant: Medtronic Ardian Luxembourg S.a.r.l., Luxembourg (LU)

(72) Inventor: Nishant R. Srivastava, Mountain View, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 14/716,167

(22) Filed: May 19, 2015

(65) Prior Publication Data

US 2015/0335263 A1 Nov. 26, 2015

Related U.S. Application Data

(63) Continuation of application No. 13/870,172, filed on Apr. 25, 2013, now Pat. No. 9,066,726.
(Continued)

(51) Int. Cl.
*A61B 18/18* (2006.01)
*A61B 5/06* (2006.01)
(Continued)

(52) U.S. Cl.
CPC ............ *A61B 5/065* (2013.01); *A61B 5/02* (2013.01); *A61B 17/320068* (2013.01); *A61B 18/14* (2013.01); *A61B 18/1492* (2013.01); *A61B 18/1815* (2013.01); *A61N 1/403* (2013.01); *A61N 5/025* (2013.01);
(Continued)

(58) Field of Classification Search
CPC ............ A61B 18/1492; A61B 2018/00434; A61B 2018/00577; A61B 2018/1435; A61B 2019/465; A61B 2018/00404; A61B 218/00511; A61B 2018/00654; A61B 2018/00214
See application file for complete search history.

(56) References Cited

U.S. PATENT DOCUMENTS

| 4,602,624 A | 7/1986 | Naples et al. |
| 4,649,936 A | 3/1987 | Ungar et al. |
(Continued)

FOREIGN PATENT DOCUMENTS

| WO | WO9407446 | 4/1994 |
| WO | WO-9525472 | 9/1995 |
(Continued)

OTHER PUBLICATIONS

European Search Report for European Application No. 13159256, Date Mailed: Oct. 17, 2013, 6 pages.
(Continued)

*Primary Examiner* — Michael Peffley
*Assistant Examiner* — Amanda Zink

(57) ABSTRACT

Apparatus and methods for determining positioning of a energy delivery element include deploying a energy delivery element at a treatment site proximal to a vessel wall; using a multi-region pressure sensing apparatus to sense pressures applied in a plurality of directions about the energy delivery element; and determining an orientation of the energy delivery element based on the pressures measured in the plurality of directions about the energy delivery element.

13 Claims, 22 Drawing Sheets

Related U.S. Application Data

(60) Provisional application No. 61/801,890, filed on Mar. 15, 2013.

(51) Int. Cl.
*A61B 18/14* (2006.01)
*A61N 1/40* (2006.01)
*A61B 17/32* (2006.01)
*A61N 5/02* (2006.01)
*A61B 5/02* (2006.01)
*A61B 18/00* (2006.01)

(52) U.S. Cl.
CPC .......... *A61B 2018/00214* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00654* (2013.01); *A61B 2018/1435* (2013.01); *A61B 2090/065* (2016.02)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele et al. |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,063,022 A * | 5/2000 | Ben-Haim ............. A61B 34/20 600/41 |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,241,724 B1 | 6/2001 | Fleischman et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto et al. |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,357,152 B2 * | 1/2013 | Govari ............. A61B 5/06 600/12 |
| 8,728,075 B2 * | 5/2014 | Wu ............. A61F 5/0013 606/33 |
| 9,101,734 B2 * | 8/2015 | Selkee ............. A61B 5/042 |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danek et al. |
| 2004/0010289 A1 | 1/2004 | Biggs et al. |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0036948 A1 | 2/2009 | Levin et al. |
| 2009/0177095 A1 * | 7/2009 | Aeby ............. A61B 5/0084 600/478 |

(56) References Cited

U.S. PATENT DOCUMENTS

| | | |
|---|---|---|
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0264086 A1* | 10/2011 | Ingle ............. A61B 18/1492 606/33 |
| 2012/0130289 A1 | 5/2012 | Demarais et al. |
| 2012/0130345 A1 | 5/2012 | Levin et al. |
| 2012/0172837 A1 | 7/2012 | Demarais et al. |

FOREIGN PATENT DOCUMENTS

| | | |
|---|---|---|
| WO | WO9531142 | 11/1995 |
| WO | WO-9736548 | 10/1997 |
| WO | WO9842403 | 10/1998 |
| WO | WO-99/00060 | 1/1999 |
| WO | WO-0122897 | 4/2001 |
| WO | WO-0170114 | 9/2001 |
| WO | WO03022167 | 3/2003 |
| WO | WO03082080 | 10/2003 |
| WO | WO2005030072 | 4/2005 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO2006105121 | 10/2006 |
| WO | WO-2007008954 | 1/2007 |
| WO | WO2007078997 | 7/2007 |
| WO | WO2008049084 | 4/2008 |

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.

(56) References Cited

OTHER PUBLICATIONS

"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

(56) References Cited

OTHER PUBLICATIONS

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rate", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

(56) References Cited

OTHER PUBLICATIONS

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16: 1 page.

Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.

Opposition to European Patent No. 2465470, Granted Oct. 28, 2015, Date of Opposition Jul. 27, 2016, 34 pp.

Pieper, et al., "Design and Implementation of a New Computerized System for Intraoperative Cardiac Mapping" Journal of Applied Physiology, 1991, vol. 71 (4), pp. 1529-1539.

Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.

U.S. Appl. No. 11/363,867, filed Feb. 27, 2006, 70 pp.
U.S. Appl. No. 60/813,589, filed Dec. 29, 2005, 62 pp.
U.S. Appl. No. 60/852,787, filed Oct. 18, 2006, 112 pp.
Ureter, https://en.wikipedia.org/wiki/Ureter, Jun. 2016, 6 pp.

* cited by examiner

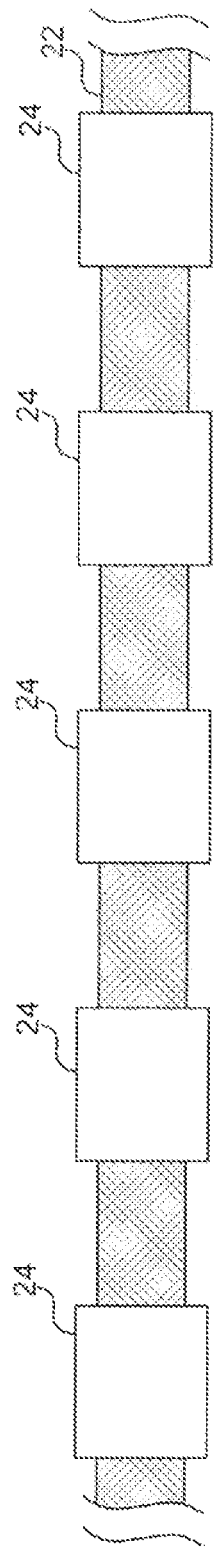
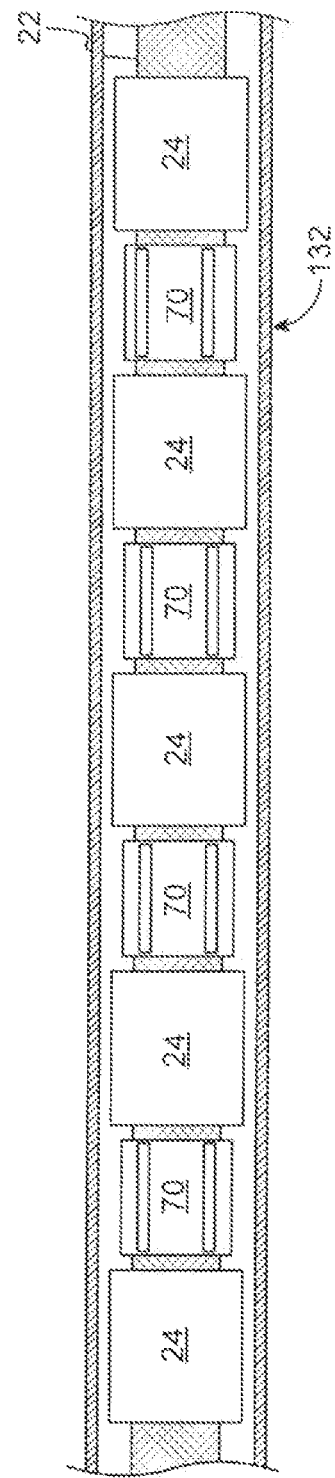

9,510,773 B2

MULTI-ELECTRODE APPOSITION JUDGMENT USING PRESSURE ELEMENTS

RELATED APPLICATIONS

This application is a continuation of U.S. patent application Ser. No. 13/870,172, filed Apr. 25, 2013, now U.S. Pat. No. 9,066,726, which claims the benefit of U.S. Provisional Patent Application No. 61/801,890 filed Mar. 15, 2013, the disclosures of both which are herein incorporated by reference in their entirety.

TECHNICAL FIELD

The present disclosure relates generally to the field of neuromodulation, and some embodiments relate to measurements and metrics for determining the efficacy of treatment More particularly, some embodiments relate to the use of pressure sensors to determine positioning of neuromodulation devices and to determine the effectiveness of renal neuromodulation treatment.

BACKGROUND

The sympathetic nervous system (SNS) is a primarily involuntary bodily control system typically associated with stress responses. Fibers of the SNS innervate tissue present in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys of plasma is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal artery (e.g., via radiofrequency ablation) have been shown to reduce blood pressure in patients with treatment-resistant hypertension.

SUMMARY

The present technology is generally directed to modulation of nerves, including nerves innervating the kidneys. Various techniques can be used to partially or completely incapacitate neural pathways, such as those innervating the kidney. The application of energy to tissue can induce the desired treatment effects. The energy can be, for example, radiofrequency energy, mechanical energy, acoustic energy, electrical energy, thermal energy, and so on. The energy can be delivered to the tissue by one or more electrodes or other energy delivery elements. The energy delivery elements can be disposed on a support structure and the support structure used to position the energy delivery elements for treatment.

In various embodiments, one or more pressure sensors are provided and disposed adjacent the one or more energy delivery elements. The pressure sensors can be used to measure attributes such as blood pressure, blood flow and pressure of energy delivery elements against a vessel wall. Multi-region sensors can be used to detect pressures in a plurality of directions.

In other embodiments, an apparatus for neuromodulation treatment can include a therapeutic assembly configured to be delivered to a treatment site within a vessel; an energy delivery element disposed on the therapeutic assembly and configured to be positioned against a vessel wall to deliver neuromodulation energy at the treatment site; and a pressure sensor disposed adjacent and in fixed relation to the energy delivery element and comprising a plurality of pressure sensitive regions. A pressure measurement circuit can also be included and coupled to the pressure sensor and configured to determine which of the plurality of pressure sensitive regions is being subjected to increased pressure.

In some embodiments, the plurality of pressure sensitive regions can be arranged to sense pressure in a plurality of radial directions relative to the energy delivery element. The plurality of pressure sensitive regions can also be configured to allow the pressure sensor to respond to pressure applied at different angles, and the apparatus can further include a pressure measurement circuit coupled to the pressure sensor and configured to determine an angle of apposition of the energy delivery element.

In some applications, the pressure sensor can include a first conductive annular ring; a second conductive annular ring disposed coaxially with the first conductive annular ring; a plurality of non-conductive areas on the second conductive annular ring, the non-conductive areas defining conductive regions about the second conductive annular ring. The non-conductive areas can include slots disposed in the second conductive annular ring, and the conductive regions can be spaced evenly about the second conductive annular ring.

The pressure sensor can include: a first hollow conductive member; a second hollow conductive member disposed coaxially within the first conductive member; a plurality of non-conductive areas on the first conductive member, the non-conductive areas defining conductive regions about the first conductive member, wherein the non-conductive areas comprise slots disposed first conductive member. The first and second hollow conductive members can be annular in shape.

In various embodiments, the energy delivery element can be an RF electrode, a thermal element, a cryo-ablation element, a microwave energy delivery element, an optical energy delivery element, or an ultrasonic transducer. The therapeutic assembly can include an elongated support structure configured to take a pre-determined shape upon deployment in a vessel, wherein the energy delivery element can be disposed in a predetermined orientation on the elongated support structure, and wherein the pressure sensor can be arranged such that the plurality of pressure sensitive regions can be configured to sense pressure in a plurality of directions about the energy delivery element. The elongated support structure can be a shape set wire set in a helical geometry or a catheter tip, for example.

In further embodiments, a method for determining positioning an energy delivery element for neuromodulation, can include deploying an energy delivery element at a treatment site proximal to a vessel wall; using a multi-region pressure sensing apparatus to sense pressures applied in a plurality of directions about the energy delivery element; and determining an orientation of the energy delivery element based on the pressures measured in the plurality of directions about the energy delivery element. Determining an orientation, can include measuring pressures applied against a plurality of pressure sensors in the multi-region pressure sensing apparatus, each sensor disposed to measure pressure impinging on the sensing apparatus at a different angle; determining based on the pressures measured which of a plurality of regions of the pressure sensing apparatus can be contacting the vessel wall; and determining an orientation of the energy delivery element based on the determination of which region of the pressure sensing apparatus can be contacting the vessel wall.

The method can include providing feedback to an operator to inform the operator when contact is made with the vessel based on sensed pressures and to inform the operator of the orientation of the energy delivery element.

In some embodiments, the multi-region pressure sensing apparatus can include: a first hollow conductive member; a second hollow conductive member disposed coaxially within the first conductive member; a plurality of non-conductive areas on the first conductive member, the non-conductive areas defining conductive regions about the first conductive member. In other embodiments, the multi-region pressure sensing apparatus includes: a first conductive annular ring; a second conductive annular ring disposed coaxially with the first conductive annular ring; a plurality of non-conductive areas on the second conductive annular ring, the non-conductive areas defining conductive regions about the second conductive annular ring.

In still further embodiments, an apparatus for neuromodulation treatment, can include a support structure configured to be delivered to a treatment site within a vessel; a plurality of energy delivery elements disposed on the support structure and configured to be positioned against a vessel wall to deliver neuromodulation energy at the treatment site; and a plurality of pressure sensor elements disposed adjacent and in fixed relation to the energy delivery elements, each pressure sensor element can include a plurality of pressure sensitive regions.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The present invention, in accordance with one or more various embodiments, is described in detail with reference to the accompanying figures. The drawings are provided for purposes of illustration only and merely depict typical or example embodiments of the invention. These drawings are provided to facilitate the reader's understanding of the systems and methods described herein, and shall not be considered limiting of the breadth, scope, or applicability of the claimed invention.

FIG. 10A is a diagram illustrating an example of a support structure with a plurality of energy delivery elements.

FIG. 10B is a diagram illustrating an example in which a plurality of pressure measurement devices are disposed on a support structure proximal to a plurality of electrodes in accordance with one embodiment of the technology disclosed herein.

Figure 1:
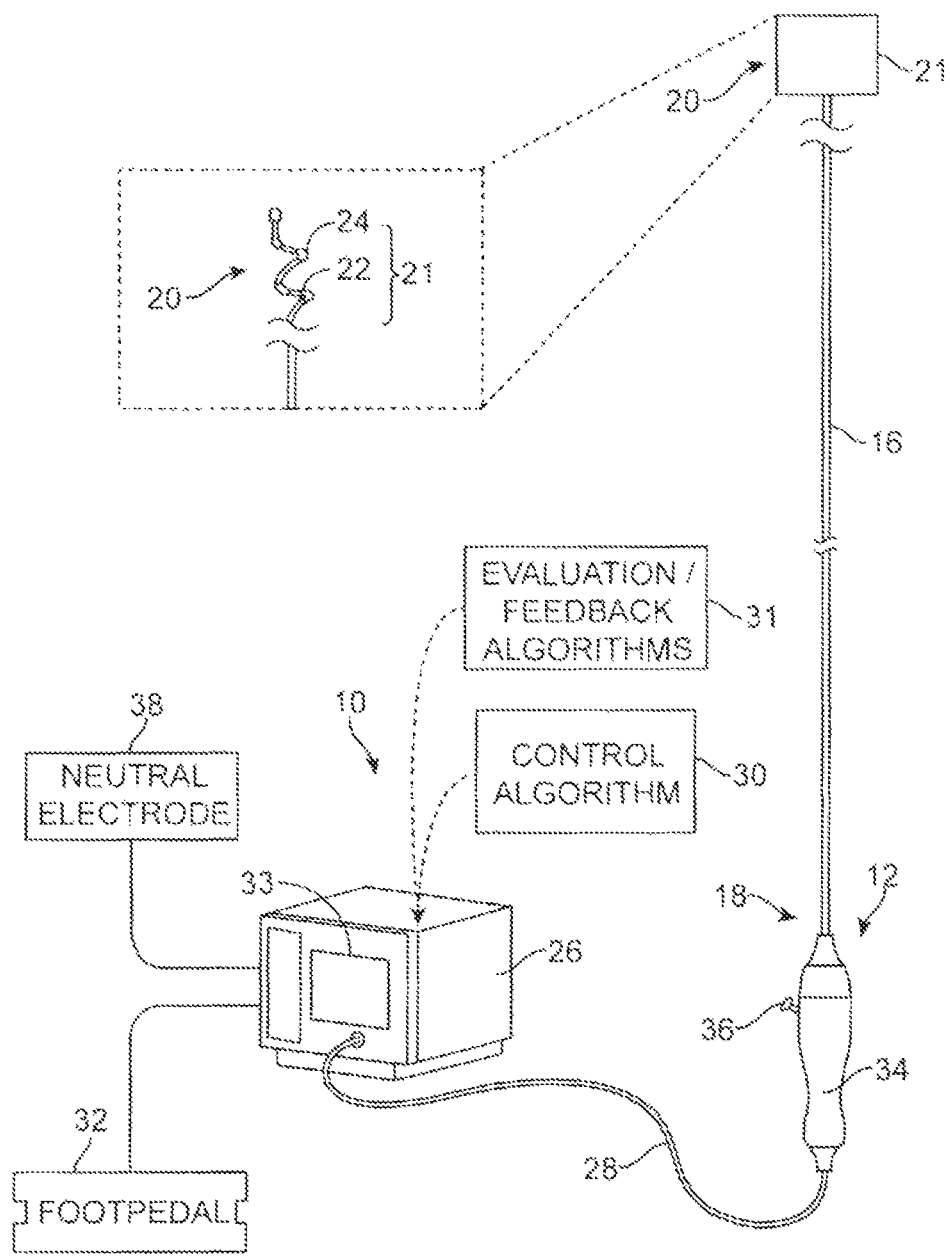
FIG. 1 illustrates a system in accordance with one embodiment of the technology disclosed herein.

The figures are not intended to be exhaustive or to limit the invention to the precise form disclosed. It should be understood that the invention can be practiced with modification and alteration, and that the invention be limited only by the claims and the equivalents thereof.

DESCRIPTION

The present technology is generally directed to modulation of nerves, including nerves innervating the kidneys. Various techniques can be used to partially or completely incapacitate neural pathways, such as those innervating the kidney. The purposeful application of energy (e.g., radiofrequency energy, mechanical energy, acoustic energy, electrical energy, thermal energy, etc.) to tissue can induce one or more desired thermal heating effects on localized regions of the renal artery and adjacent regions of the renal plexus (RP), which lay intimately within or adjacent to the adventitia of the renal artery. The purposeful application of the thermal heating and cooling effects can achieve neuromodulation along all or a portion of the renal plexus (RP).

Specific details of several embodiments of the present technology are described herein with reference to the accompanying figures. Although many of the embodiments are described herein with respect to cryotherapeutic, electrode-based, transducer-based, and chemical-based approaches, other treatment modalities in addition to those described herein are within the scope of the present technology. Additionally, other embodiments of the present technology can have configurations, components, or procedures different from those described herein. For example, other embodiments can include additional elements and features beyond those described herein or be without several of the elements and features shown and described herein. Generally, unless the context indicates otherwise, the terms "distal" and "proximal" within this disclosure reference a position relative to an operator or an operator's control device. For example, "proximal" can refer to a position closer to an operator or an operator's control device, and "distal" can refer to a position that is more distant from an operator or an operator's control device. The headings provided herein are for convenience only.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis and sudden death. The reduction of afferent neural signals contributes to the systemic reduction of sympathetic tone/drive, and renal neuromodulation is expected to be useful in treating several conditions associated with systemic sympathetic overactivity or hyper-activity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics.

Various techniques can be used to partially or completely incapacitate neural pathways, such as those innervating the kidney. The purposeful application of energy (e.g., electrical energy, thermal energy) to tissue by energy delivery element(s) can induce one or more desired thermal heating effects on localized regions of the renal artery and adjacent regions of the renal plexus RP, which lay intimately within or adjacent to the adventitia of the renal artery. The purposeful application of the thermal heating effects can achieve neuromodulation along all or a portion of the renal plexus RP.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected.

II. Selected Embodiments of Treatment Systems

FIG. 1 illustrates a system 1 in accordance with an embodiment of the present technology. The system 1 includes a renal neuromodulation system 10 ("system 10"). The system 10 includes an intravascular or intraluminal treatment device 12 that is operably coupled to an energy source or console 26. Energy source or console 26 can include, for example, an RF energy generator, a cryotherapy console, an ultrasonic signal generator or other energy source. Energy source or console 26 can also include a source of drugs or other substances used for chemical neuromodulation. In the embodiment shown in FIG. 1, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a therapeutic assembly or treatment section 21 at the distal portion 20 of the shaft 16. The therapeutic assembly 21 can include a neuromodulation assembly (e.g., actuators such as one or more electrodes or energy delivery elements, a cryotherapeutic cooling assembly, etc.). The therapeutic assembly 21 can include virtually any suitable energy delivery device configured to cause therapeutically effective nerve modulation, such as cryotherapeutic catheters, single- or multi-electrode neuromodulation devices, or ultrasound transducers.

As explained in further detail below, and as shown in the insert of FIG. 1, the therapeutic assembly 21 in some embodiments can include an array of two or more electrodes or energy delivery elements 24 configured to be delivered to a renal blood vessel (e.g., a renal artery) in a low-profile configuration. Upon delivery to the target treatment site within the renal blood vessel, the therapeutic assembly 21 is further configured to be deployed into an expanded state (e.g., a generally helical or spiral configuration as shown in the insert) for delivering energy at the treatment site and providing therapeutically-effective electrically- and/or thermally induced renal neuromodulation. Alternatively, the deployed state may be non-helical provided that the deployed state delivers the energy to the treatment site.

In some embodiments, the therapeutic assembly 21 may be placed or transformed into the deployed state or arrangement via remote actuation, e.g., via an actuator 36, such as a knob, button, pin, or lever carried by the handle 34. In other embodiments, however, the therapeutic assembly 21 may be transformed between the delivery and deployed states using other suitable mechanisms or techniques.

The proximal end of the therapeutic assembly 21 is carried by or affixed to the distal portion 20 of the elongated shaft 16. A distal end of the therapeutic assembly 21 may terminate with, for example, an atraumatic rounded tip or cap. Alternatively, the distal end of the therapeutic assembly 21 may be configured to engage another element of the system 10 or treatment device 12. For example, the distal end of the therapeutic assembly 21 may define a passageway for engaging a guide wire (not shown) for delivery of the treatment device using over-the-wire ("OTW") or rapid exchange ("RX") techniques.

The energy source or console 26 is configured to generate a selected form and magnitude of energy for delivery to the target treatment site via the therapeutic assembly 21. Particularly, in some embodiments, an RF energy generator can be configured to generate a selected form and magnitude of energy for delivery to the target treatment site via the energy delivery elements 24. The energy generator 26 can be electrically coupled to the treatment device 12 via a cable 28. At least one supply wire (not shown) passes along the elongated shaft 16 or through a lumen in the elongated shaft 16 to the energy delivery elements 24 and transmits the treatment energy to the energy delivery elements 24. In some embodiments, each energy delivery element 24 includes its own supply wire. In other embodiments, however, two or more energy delivery elements 24 may be electrically coupled to the same supply wire.

A control mechanism, such as foot pedal 32 or other operator control, may be connected (e.g., pneumatically connected or electrically connected) to the console to allow the operator to initiate, terminate and, optionally, adjust various operational characteristics of the energy generator, including, but not limited to, power delivery.

The system 10 may also include a remote control device (not shown) that can be positioned in a sterile field and operably coupled to the therapeutic assembly 21. The remote control device can be configured to allow for selective activation of the therapeutic assembly 21, such as selectively turning off and on energy delivery elements 24. For example, the remote control device can be configured to allow the operator to initiate, terminate and, optionally, adjust various operational characteristics of the energy generator. In some embodiments, a control mechanism (not shown) may be built into the handle assembly 34 allowing operator control through actuation of buttons, switches or other mechanisms on the handle assembly 34.

Figure 2:
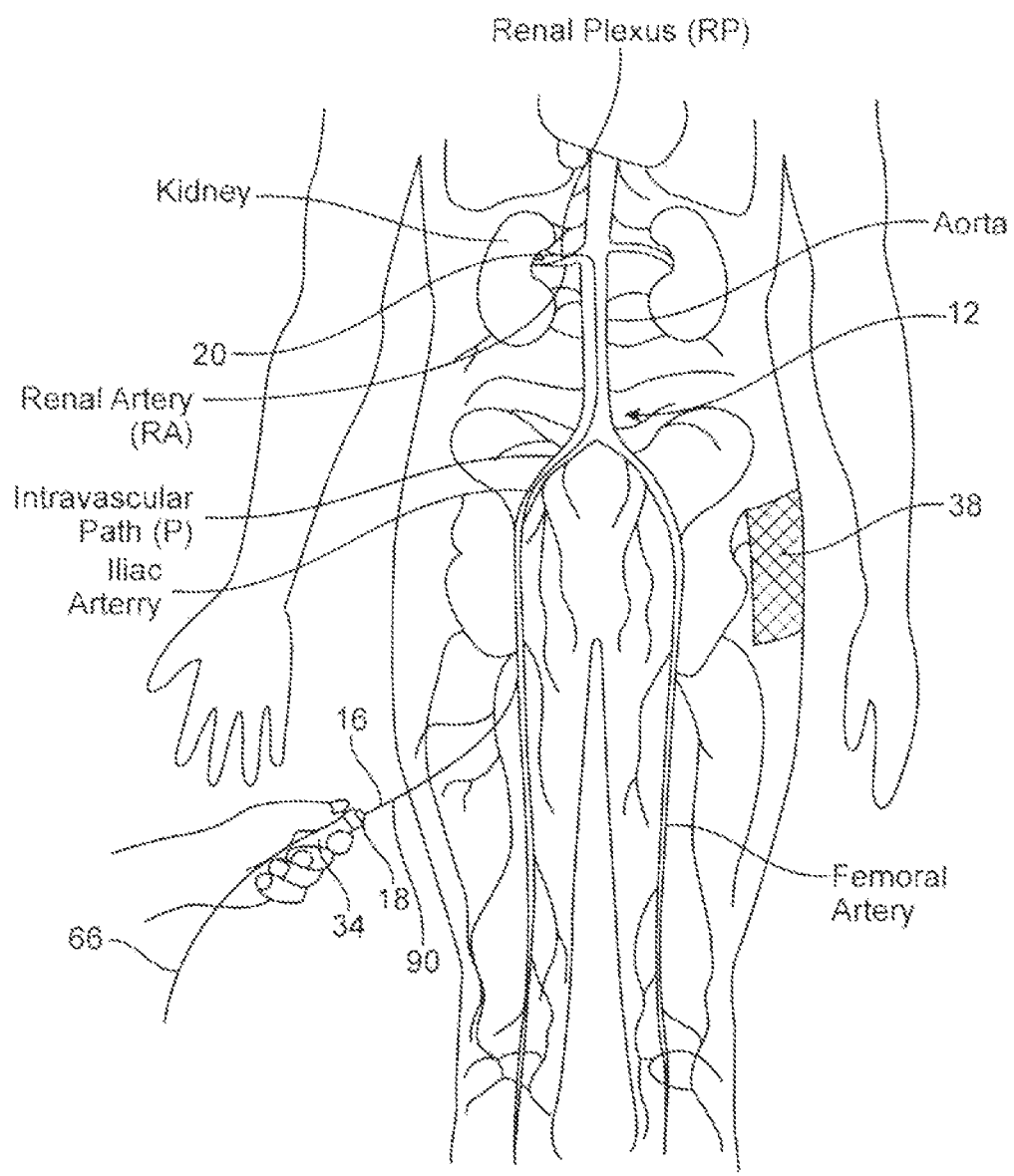
FIG. 2 illustrates one example of modulating renal nerves with an embodiment of the system described with reference to FIG. 1.

In some embodiments, the system 10 may be configured to provide delivery of a monopolar electric field via the energy delivery elements 24. In such embodiments, a neutral or dispersive electrode 38 may be electrically connected to the energy generator 26 and attached to the exterior of the patient (as shown in FIG. 2). Additionally, one or more sensors (not shown), such as one or more temperature (e.g., thermocouple, thermistor, etc.), impedance, pressure, optical, flow, chemical or other sensors, may be located proximate to or within the energy delivery elements 24 and connected to one or more supply wires (not shown). For example, a total of two supply wires may be included, in which both wires could transmit the signal from the sensor and one wire could serve dual purpose and also convey the energy to the energy delivery elements 24. Alternatively, a different number of supply wires may be used to transmit energy to the energy delivery elements 24.

The energy source 26 can be configured to deliver the treatment energy under the control of an automated control algorithm 30, under the control of the clinician, or via a combination thereof. In addition, the energy source or console 26 may include one or more evaluation or feedback algorithms 31 that can be configured to accept information and provide feedback to the clinician before, during, and/or after therapy (e.g., neuromodulation). Feedback can be provided in the form of audible, visual or haptic feedback. The feedback can be based on output from a monitoring system (not shown). The monitoring system can be a system including sensors or other monitoring devices integrated with treatment device 12, sensors or other monitoring devices separate from treatment device 12, or a combination thereof. The monitoring devices of the monitoring system can be configured to measure conditions at the treatment site (e.g., the temperature of the tissue being treated), systemic conditions (e.g., patient vital signs), or other conditions germane to the treatment or to the health and safety of the patient.

The energy source 26 can further include a device or module that may include processing circuitry, such as one or more microprocessors and associated memory. The processing circuitry may be configured to execute stored instructions relating to the control algorithm 30, the evaluation/feedback algorithm 31 and other functions of the device. The energy source 26 may be configured to communicate with the treatment device 12 (e.g., via the cable 28) to control the neuromodulation assembly and/or to send signals to or receive signals from the monitoring system. The display 33 may be configured to provide indications of power levels or sensor data, such as audio, visual or other indications, or may be configured to communicate the information to another device. For example, the console 26 may also be operably coupled to a catheter lab screen or system for displaying treatment information (e.g., nerve activity before and after treatment, effects of ablation, efficacy of ablation of nerve tissue, lesion location, lesion size, etc.).

The energy source or console 26 can be configured to control, monitor, supply, or otherwise support operation of the treatment device 12. In other embodiments, the treatment device 12 can be self-contained and/or otherwise configured for operation without connection to the energy source or console 26. As shown in the example of FIG. 1, the energy source or console 26 can include a primary housing having a display 33.

Furthermore, the energy source or console 26 can be configured to communicate with the treatment device 12, e.g., via the cable 28. For example, the therapeutic assembly 21 of the treatment device 12 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 34. The cable 28 can be configured to carry the signal from the handle 34 to the energy source or console 26.

The energy source or console 26 can have different configurations depending on the treatment modality of the treatment device 12. For example, when the treatment device 12 is configured for electrode-based or transducer-based treatment, the energy source or console 26 can include an energy generator (not shown) configured to generate RF energy, pulsed RF energy, microwave energy, optical energy, focused ultrasound energy (e.g., high-intensity focused ultrasound energy), direct heat energy, or another suitable type of energy. In some embodiments, the energy source or console 26 can include a RF generator operably coupled to one or more electrodes (not shown) of the therapeutic assembly 21.

As a further example, in embodiments where the treatment device 12 is configured for cryotherapeutic treatment, the energy source or console 26 can include a refrigerant reservoir (not shown) and can be configured to supply the treatment device 12 with refrigerant, e.g., pressurized refrigerant in liquid or substantially liquid phase. Similarly, in embodiments where the treatment device 12 is configured for chemical-based treatment, the energy source or console 26 can include a chemical reservoir (not shown) and can be configured to supply the treatment device 12 with the chemical. In some embodiments, the treatment device 12 can include an adapter (not shown) (e.g., a luer lock) configured to be operably coupled to a syringe (not shown). The adapter can be fluidly connected to a lumen (not shown) of the treatment device 20, and the syringe can be used, for example, to manually deliver one or more chemicals to the treatment location, to withdraw material from the treatment location, to inflate a balloon (not shown) of the therapeutic assembly 21, to deflate a balloon of the therapeutic assembly 21, or for another suitable purpose. In other embodiments, the energy source or console 26 can have other suitable configurations.

FIG. 2 illustrates one example of modulating renal nerves with an embodiment of the system 10. In this embodiment, the treatment device 12 provides access to the renal plexus (RP) through an intravascular path (P), such as a percutaneous access site in the femoral (illustrated), brachial, radial, or axillary artery to a targeted treatment site within a respective renal artery (RA). As illustrated, a section of the proximal portion 18 of the shaft 16 is exposed externally of the patient. By manipulating the proximal portion 18 of the shaft 16 from outside the intravascular path (P), the clinician may advance the shaft 16 through the sometimes tortuous intravascular path (P) and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12 itself.

After the therapeutic assembly 21 is adequately positioned in the renal artery (RA), it can be radially expanded or otherwise deployed using the handle 34 or other suitable means until the neuromodulation assembly (e.g., energy delivery elements 24) is positioned at its target site in stable contact with the inner wall of the renal artery (RA). The purposeful application of energy from the neuromodulation assembly (e.g., from energy delivery elements 24) is then applied to tissue to induce one or more desired neuromodulating effects on localized regions of the renal artery and adjacent regions of the renal plexus (RP), which lay intimately within, adjacent to, or in close proximity to the adventitia of the renal artery (RA). The purposeful application of the energy may achieve neuromodulation along all or at least a portion of the renal plexus (RP).

The neuromodulating effects are generally a function of, at least in part, power, time, contact between the energy delivery elements 24 and the vessel wall, and blood flow through the vessel. The neuromodulating effects may include denervation, thermal ablation, and non-ablative thermal alteration or damage (e.g., via sustained heating and/or resistive heating).

The energy delivery elements of the therapeutic assembly 21 may be proximate to, adjacent to, or carried by (e.g., adhered to, threaded over, wound over, and/or crimped to) a support structure. In some embodiments, the therapeutic assembly 21 defines a substantially helical support structure that can be delivered to the treatment site in a low-profile or collapsed state, and expanded at the treatment site to contact the renal artery wall along a helical path. One example of a helical support structure includes a pre-shaped helical section wound around a central lumen. A straightening guide wire can be provided and inserted into the lumen to force the helical section into a straightened, delivery configuration. Withdrawal of the guide wire allows the helical section to expand making contact with vessel walls.

Figure 3:
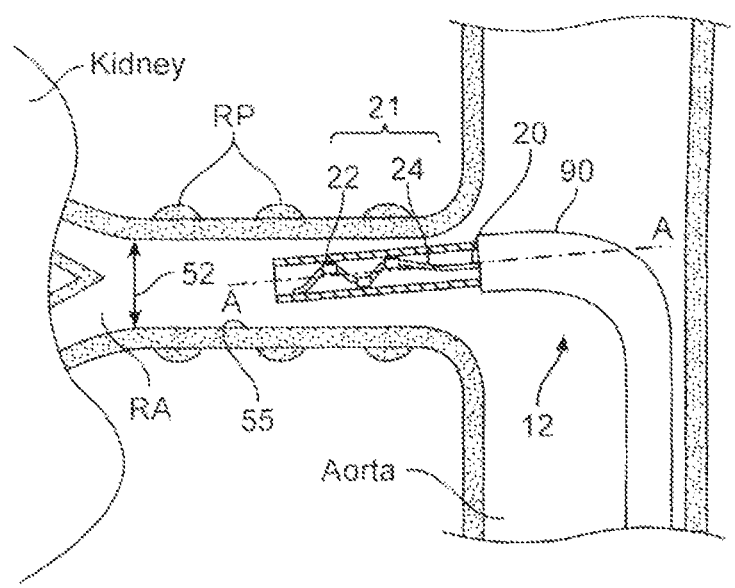
FIG. 3 illustrates a cross-sectional view of one embodiment of a therapeutic assembly defining a helical support structure in a delivery state within a renal artery.
Figure 4:
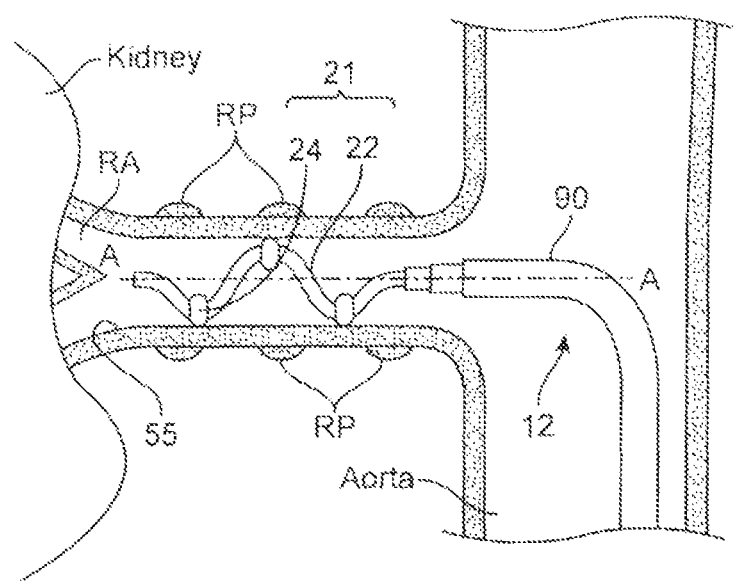
FIG. 4 illustrates the example therapeutic assembly 21 of FIG. 3 in an expanded state within the renal artery.

FIGS. 3 and 4 illustrate an example embodiment in which the support structure is in a helical configuration. FIG. 3 is a cross-sectional view illustrating one embodiment of therapeutic assembly 21 defining a helical support structure in a delivery state (e.g., low-profile or collapsed configuration) within a renal artery RA. FIG. 4 illustrates this example therapeutic assembly 21 in an expanded state (e.g., expanded or helical configuration) within the renal artery RA.

Referring first to FIG. 3, the delivery arrangement of the therapeutic assembly 21 defines a low profile about the longitudinal axis A-A of the assembly such that a transverse dimension of the therapeutic assembly 21 is sufficiently small to define a clearance distance between an arterial wall 55 and the treatment device 12. The delivery state facilitates insertion and/or removal of the treatment device 12 and, if desired, repositioning of the therapeutic assembly 21 within the renal artery RA. In the collapsed configuration, for example, the geometry of the support structure 22 facilitates movement of the therapeutic assembly 21 through a guide catheter 90 to the treatment site in the renal artery RA.

After locating the therapeutic assembly 21 in the renal artery RA, the therapeutic assembly 21 is transformed from its delivery state to its deployed state or deployed arrangement. As shown in FIG. 4, therapeutic assembly 21 is expanded within the renal artery RA such that the energy delivery elements 24 are in contact with the renal artery wall 55. In some embodiments, manipulation of the distal portion 20 also facilitates contact between the energy delivery elements 24 and the wall of the renal artery.

Alignment of the assembly may include alignment of geometrical aspects of the energy delivery elements 24 with the renal artery wall 55. For example, in embodiments in which the energy delivery elements 24 have a cylindrical shape with rounded ends, alignment may include alignment of the longitudinal surface of the individual energy delivery elements 24 with the artery wall 55. In another example, an embodiment may comprise energy delivery elements 24 having a structured shape or inactive surface, and alignment may include aligning the energy delivery elements 24 such that the structured shape or inactive surface is not in contact with the artery wall 55. In yet another example, an embodiment may comprise energy delivery elements 24 having a relatively flat energy delivery surface, and alignment may include aligning the energy delivery elements 24 such that the flat energy delivery surface is in stable contact with the artery wall 55.

Examples of helical support structures 22 that are suitable for use with the disclosed technology are described in more detail in U.S. patent application Ser. No. 13/281,360, filed Oct. 25, 2011; U.S. patent application Ser. No. 13/281,361, filed Oct. 25, 2011; and U.S. patent application Ser. No. 13/281,395, filed Oct. 25, 2011, each of which are incorporated by reference herein in their entirety.

One feature of the expanded therapeutic assembly 21 in the helical configuration is that the energy delivery elements 24 associated with the helical structure may be placed into stable contact with a vessel wall to reliably create consistent lesions. The orientation and pressure of the helical support structure 22 may be assessed in vivo by one or more pressure transducers, as discussed more fully below.

In various embodiments, one or more sensors can be included with or disposed on support structure 22 to sense conditions before, during and after renal neuromodulation. For example, pressure sensors, temperature sensors, flow sensors and the like can be included. In some embodiments, for example, a multi-region pressure sensing apparatus can be used to measure pressure impinging on the device at different angles. Such a multi-region pressure sensing apparatus can include a plurality of individual pressure sensors (or different pressure sensing regions) disposed about a central body so that each sensor (e.g., region) measures pressure impinging on the device at a different angle. A few examples of such intra-vascular pressure measurement devices are now described.

Figure 5:
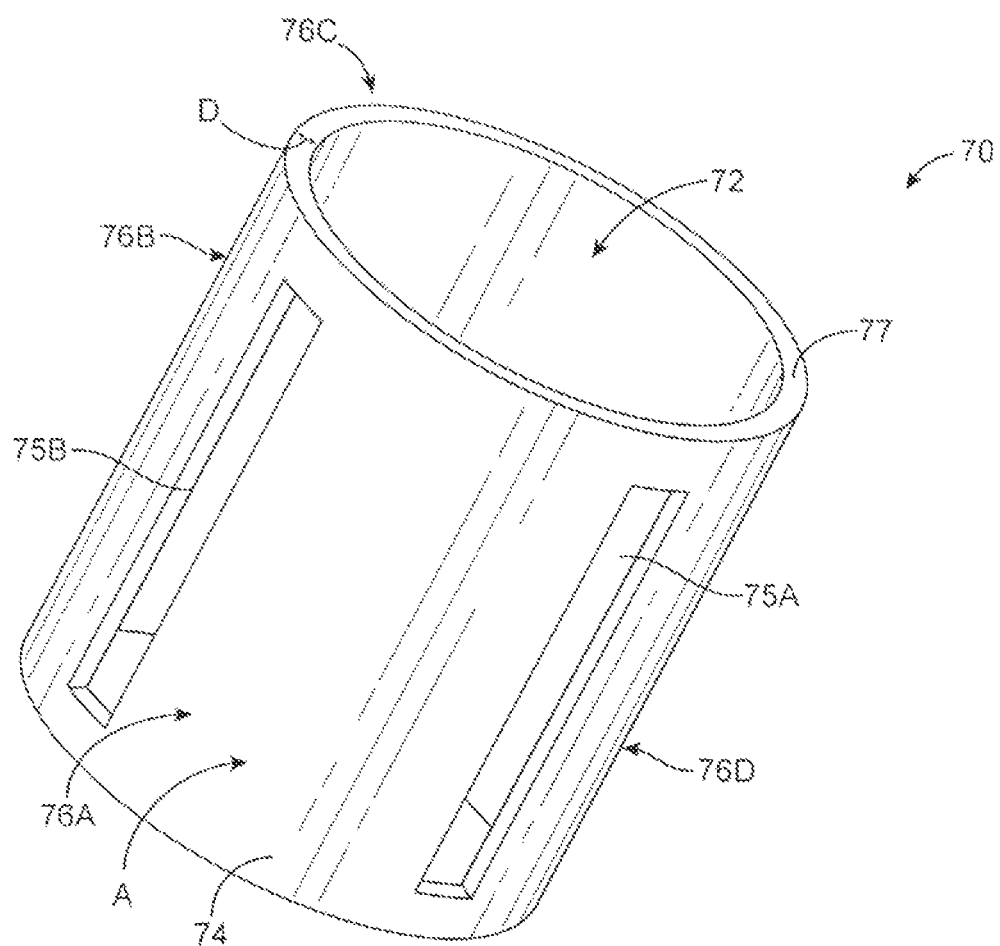
FIG. 5 is a diagram illustrating an example pressure measurement device in accordance with one embodiment of the technology disclosed herein.

One such exemplary device is illustrated in FIG. 5. The pressure measurement device 70 illustrated in FIG. 5 comprises two annular rings 72, 74 assembled in a coaxial configuration forming a hollow cylindrical unit. Inner annular ring 72 is made of a conductive material forming a continuous or substantially continuous annular ring. Outer annular ring 74 is also made of a conductive material forming an annular ring having a diameter greater than that of inner annular ring. Inner and outer annular rings 72, 74, are separated from each other by a distance, D. In one embodiment, distance D is constant about the circumference of the annular rings 72, 74, while in other embodiments, distance D can vary. The space between annular rings 72, 74 is filled with a compressible material, such that pressure exerted on outer annular ring 74 can cause outer annular ring 74 to deform, narrowing the distance D between inner and outer annular rings 72, 74. As described more fully below, inner and outer annular rings 72, 74 function as plates of a capacitor. Accordingly, the compressible material disposed between inner and outer annular rings 72, 74 can be chosen with suitable dielectric properties. In one embodiment, air is the compressible fluid used to fill the space between inner and outer annular rings 72, 74, however, other compressible dielectrics can be used, including, for example, elastomeric materials. Where air is used, non-conductive spacers can be included between inner and outer annular rings 72, 74 to prevent the rings from electrically shorting. In some embodiments, the spacers are positioned about the edge of the inner and outer annular rings 72, 74 so as to not inhibit compression of the outer annular ring 74.

Examples of conductive materials that can be used for inner and outer annular rings 72, 74 include Cu, Ag, Au, NiTi, and TiN. Any of a number of conductive materials can be used to make inner and outer annular rings 72, 74, however, for intra-vascular applications, materials with good biocompatibility are preferred.

Although the conductive plates of the pressure sensing apparatus are shown as cylindrical in this example, other hollow shapes can be used. For example four or six-sided concentric hollow members can be used, creating four or six capacitance regions, respectively.

In the example embodiment illustrated in FIG. 5, outer annular ring 74 also includes slots 75A, 75B. Slots 75A, 75B define a region 76A therebetween. In one embodiment, outer annular ring 74 includes four slots, although a fewer or greater number of slots can be provided. For example, in some embodiments two slots are provided separating the outer annular ring 74 into two separate regions. In other embodiments, five or more slots are provided, separating the outer annular ring 74 into five or more regions, respectively. The slots divide outer annular ring 74 into a plurality of separate conductive areas, thereby defining separate capacitive elements or plates. For example, in an embodiment where outer annular ring 74 in FIG. 5 includes four slots (only two of which are visible in FIG. 5), four separate conductive regions 76A, 76B, 76C, 76D are defined, creating four capacitors whose capacitance can vary individually with pressure.

The capacitance of each region is given by:

$$C = \frac{\varepsilon_r \varepsilon_0 A}{D}$$

Where A is the area of the plates, D is the distance between the plates, $\varepsilon_r$ is the relative permittivity of the dielectric material between the plates, and $\varepsilon_0$ is the permittivity of free space ($\varepsilon_0 \approx 8.854 \times 10^{-12}$ F/m).

For the sensor illustrated in FIG. 5, the area, A, is approximately the area of the outer annular ring 74 between two slots (e.g., area A is visible in FIG. 5). Because the area and the permittivities are known, the capacitance of the device can be measured to determine the distance D between the plates. The device can be calibrated and the determined distance D used to determine the amount of external pressure applied to the outer annular ring 74.

While in some embodiments absolute pressure measurement can be used, for purposes of other embodiments, what is important is measuring relative pressure changes. Relative pressure changes can be determined by measuring changes in capacitance. Changes in pressure on outer annular ring 74 are sensed based on changes in capacitance of a region of the ring that correspond to changes in the plate separation, D. A physical change in pressure causes the separation distance D to change by a quantity, Δ. Such changes can occur, for example by a change in blood pressure, or by positioning of the ring against the vessel wall or other tissue. When such changes occur, the capacitance changes from $$C = \frac{\varepsilon_r \varepsilon_0 A}{D} \text{ to } C = \frac{\varepsilon_r \varepsilon_0 A}{D + \Delta}.$$

Accordingly, measuring changes in capacitance can provide information regarding positioning of the device and changes in blood pressure. Note that because the areas of the inner and outer annular rings 72, 74 remain constant, and the permittivity of the material in the gap also remains constant, any change in capacitance can be attributed to a change in distance, D, between inner and outer annular rings 72, 74. Therefore, the equation above can be simplified to:

$$C \propto \frac{1}{D}$$

Figure 6A:
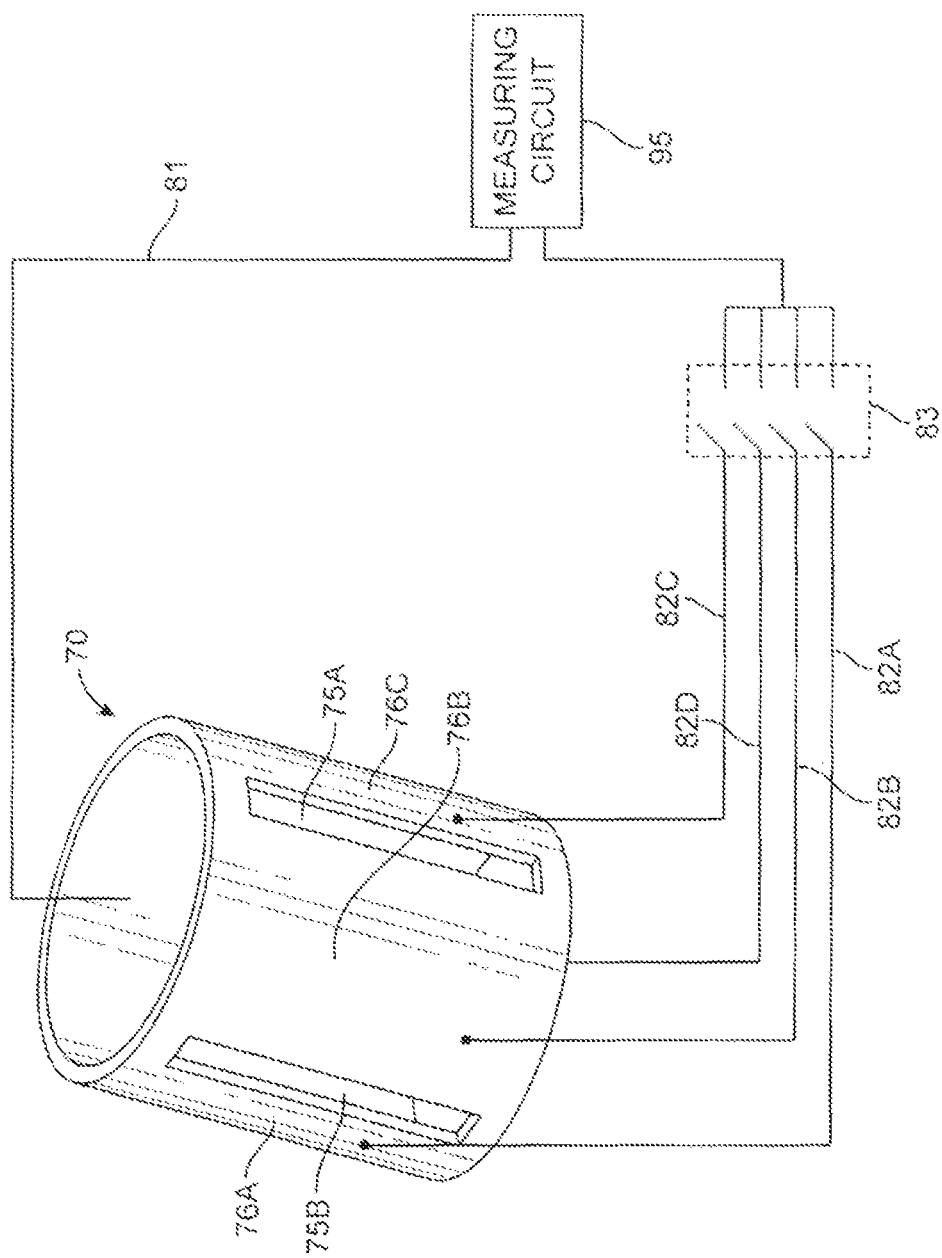
FIG. 6A illustrates an example of a pressure measurement device electrically connected to a measuring circuit in accordance with one embodiment of the technology disclosed herein.

As stated above, multiple slots can be provided in outer annular ring 74 to provide multiple individual capacitors about the circumference of the cylinder. FIG. 6A illustrates an example of a pressure measurement device 70 having four slots 75 (only two of which, 75A, 75B can be seen on the illustration), four areas 76 (only three of which 76A, 76B, 76C can be seen on the illustration) forming plates of four capacitive elements, and a measuring circuit 95. Measuring circuit 95 can be implemented using the circuits shown in FIGS. 6B and 6C, however, in other embodiments, other measuring circuits can be used.

In the example illustrated in FIG. 6A, there are four conductive paths 82A, 82B, 82C and 82D each electrically connecting its respective outer plate 76A, 76B, 76C, 76C of the corresponding capacitive element. Switches 83 are provided to selectively switch one of the four capacitive elements to measuring circuit 95. Switches can be manually actuated or they can be controlled by algorithms (e.g., by evaluation/feedback algorithms 30) to select which capacitive element is being measured. In another embodiment, multiple measuring circuits can be provided to allow simultaneous measurement of capacitive elements without the need for switching.

Figure 6B:
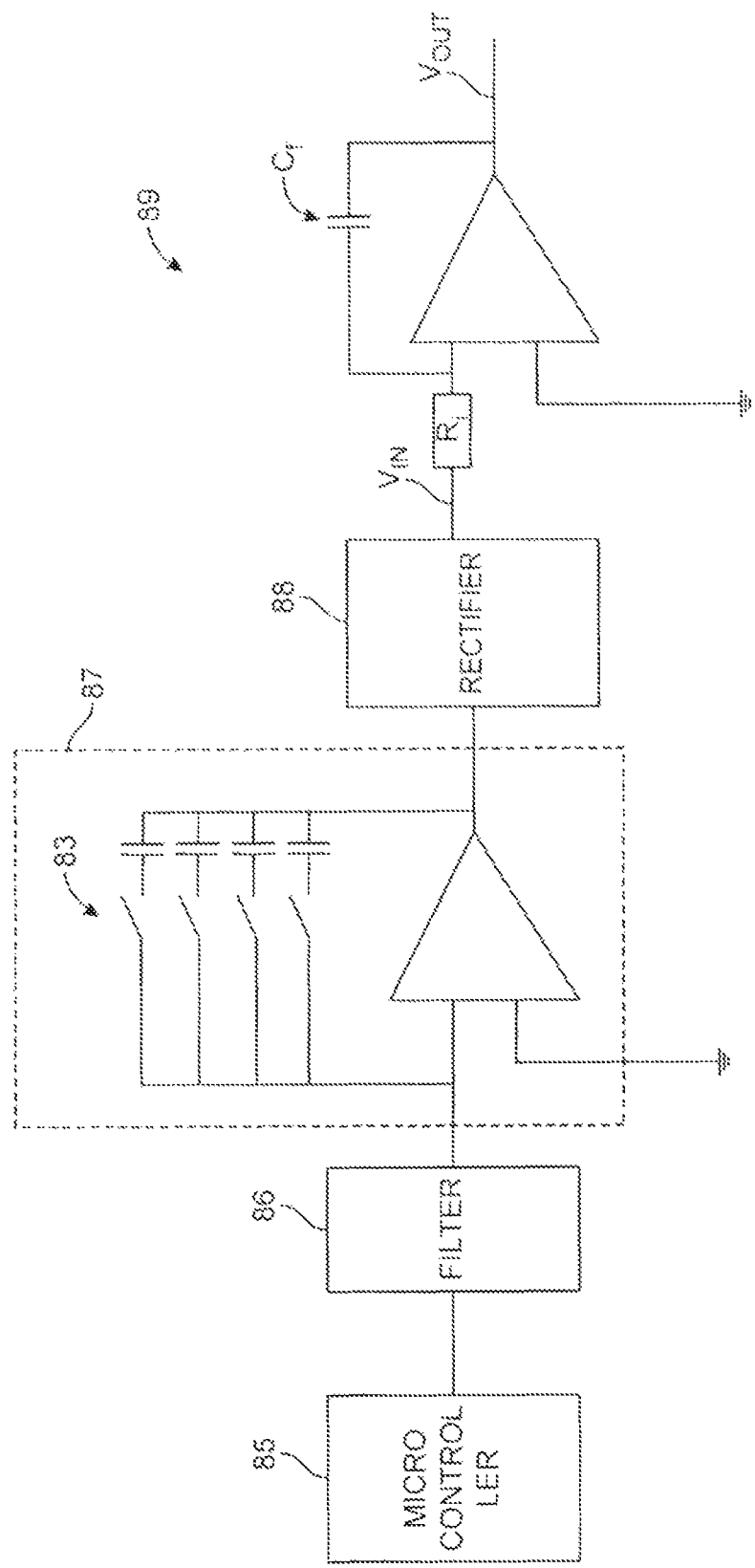
FIG. 6B is a diagram illustrating an example of a circuit that can be used to measure changes in capacitance in accordance with one embodiment of the technology disclosed herein.

FIG. 6B is a diagram illustrating an exemplary simplified circuit that can be used to measure changes in capacitance C. Referring now to FIG. 6B, in this example, a microcontroller 85 can be provided to generate a square wave. The square wave output can be filtered by filter 86 to generate a sinusoidal signal. Other signal generators can be used to generate the sinusoidal signal. The capacitor to be measured (e.g., from sensor 70) is switched into the amplifier circuit 87 by multiplexer 83. The value of the capacitance switched in to the amplifier circuit 87 affects the amplitude of the output sinusoidal signal. Rectifier 88 rectifies the sinusoid output sinusoidal signal. Rectifier 88 rectifies the sinusoid to provide a positive amplitude signal $V_{IN}$ to integrator 89. Integrator 89 charges capacitor $C_f$ over N cycles of the rectified signal and outputs a voltage $V_{OUT}$ that corresponds to the pressure value. Particularly, $$V_{OUT} = -\frac{1}{R_i C_f} \int V_{IN} dt$$

Figure 6C:
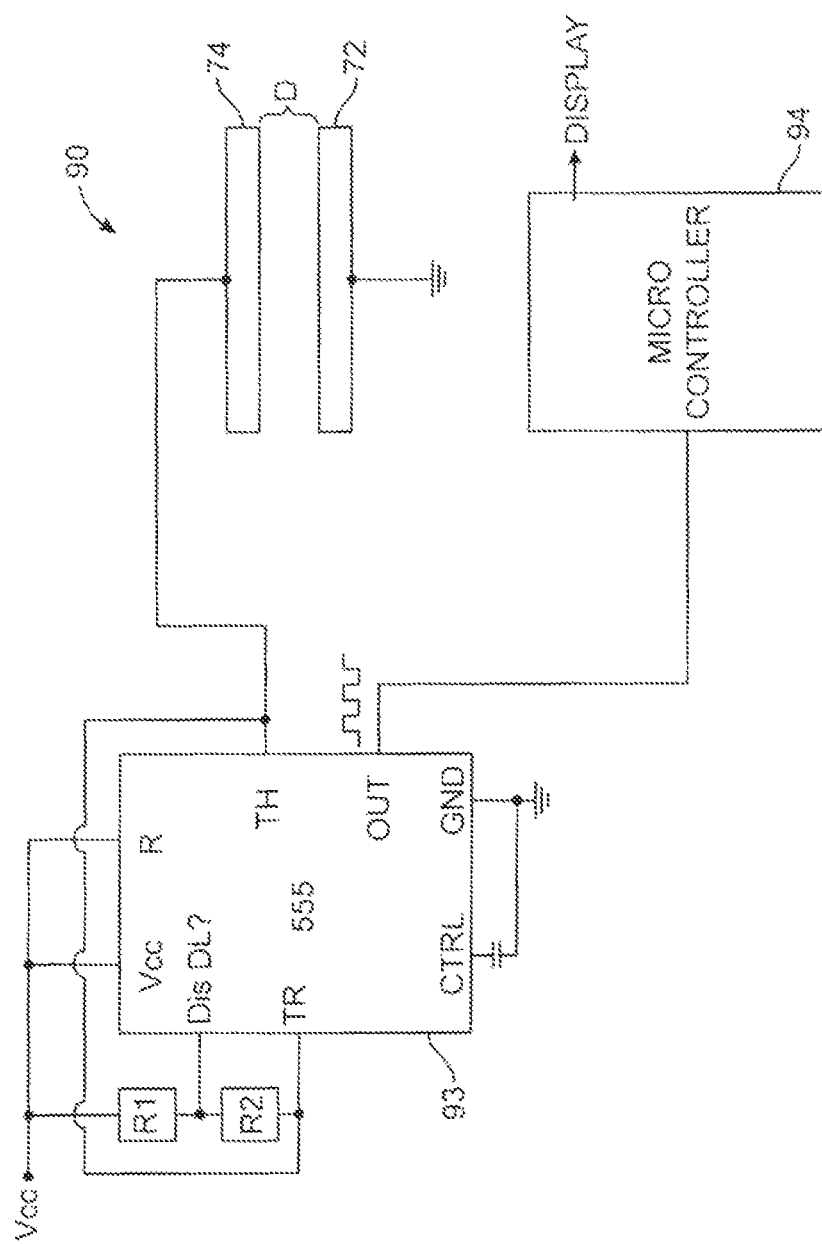
FIG. 6C is a diagram illustrating another exemplary circuit that can be used to measure changes in capacitance in accordance with one embodiment of the technology disclosed herein.

FIG. 6C is a diagram illustrating another exemplary simplified circuit that can be used to measure changes in capacitance C. This example uses a 555 timer IC 93 operating as an oscillator in the astable mode, although other oscillator circuits can be used. The variable capacitor provided by the inner and outer annular rings 72, 74, separated by a distance D is illustrated at 90. In this example, a simple timer circuit is used to generate a signal to charge and discharge the capacitor 90. The capacitor 90 is charged by the voltage applied through resistors R1 and R2. The capacitor 90 is discharged via the discharge pin DIS through resistor R2. When capacitor 90 charges and the voltage across capacitor 90 is greater than the control voltage (which with the 555 IC 93 can be controlled by control voltage pin CTRL), the output OUT transitions to a low state and the capacitor is discharged via discharge pin DIS through resistor R2. When the voltage across the capacitor 90 drops below a certain threshold (e.g., ½ of the control voltage), this voltage, applied to the trigger pin TR of IC 93, causes the output OUT to transition high and start a new timing interval. Accordingly, output pin OUT generates a square wave output whose frequency, f, varies as a function of capacitance 90 and resistances R1 and R2. Particularly, the frequency, f, of the output signal is given by the equation:

$$f = \frac{1}{C*(R1+2R2)*\ln(2)}$$

Accordingly, a microcontroller or other computing module can be used to measure the frequency, f, of the output signal and determine the capacitance of capacitor 90. Note, that although the inner annular ring 72 is shown as being connected to ground GND in this sample circuit, one of ordinary skill in the art after reading this description will understand that the polarity of the inner and outer annular rings 72, 74 can be reversed.

Figure 7A:
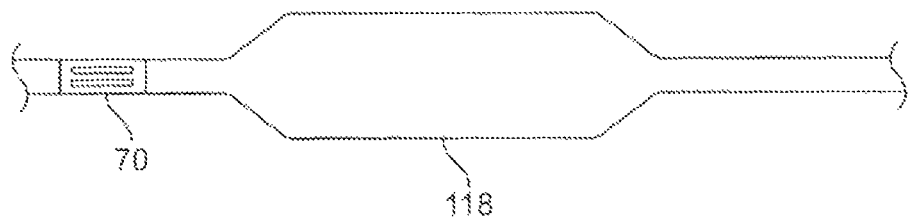
FIGS. 7A-7D provide examples of the application of one or more pressure measurement devices proximal to a therapeutic assembly to provide pressure measurements in accordance with embodiments of the technology disclosed herein.
Figure 7B:
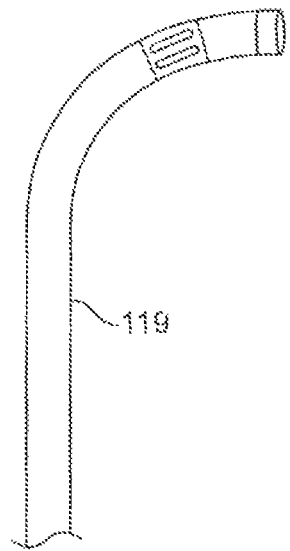
Figure 7C:
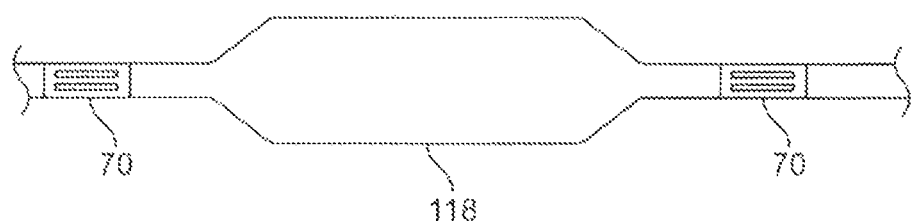
Figure 7D:
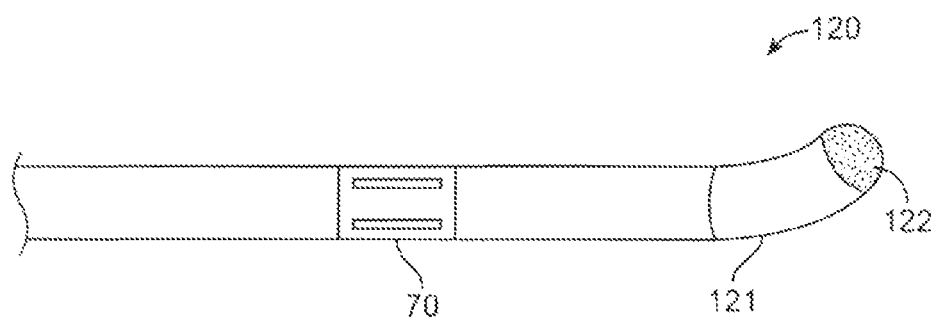

One or more pressure measurement devices 70 can be provided with treatment device 12 or therapeutic assembly 21 to measure absolute pressure or changes in pressure. FIGS. 7A-7D provide examples of using one or more pressure measurement devices (e.g., capacitance devices) 70 proximal to therapeutic assembly 21 to provide pressure measurements. FIG. 7A illustrates a pressure measurement device 70 proximal to a balloon 118. Balloon 118 can be a cryo-ablation balloon, which can be used for cryogenic treatment. Balloon 118 can also be, for example, a balloon configured to position electrodes for RF ablation, a balloon with electrodes disposed on its surface, a balloon used to place a stent, a balloon used to clear blockages, or other therapeutic balloon used for treatment. FIG. 7B illustrates a pressure measurement device 70 proximal to the distal end of a guide catheter 119. Catheter 119 can be any of a number of different types of catheter. FIG. 7C illustrates a pressure measurement device 70 positioned on both the distal and proximal ends of a balloon 118. The configuration in FIG. 7C can be used, for example, to confirm the creation of an occlusion in the vessel. FIG. 7D illustrates a pressure measurement device 70 proximal to the distal end of an RF ablation device 120. RF ablation device 120 in this example includes a flexible tip 121 and an RF probe 122 to deliver RF energy to the treatment site. The configuration illustrated in FIG. 7D can be used to provide real time blood pressure monitoring during RF ablation.

Figure 8A:
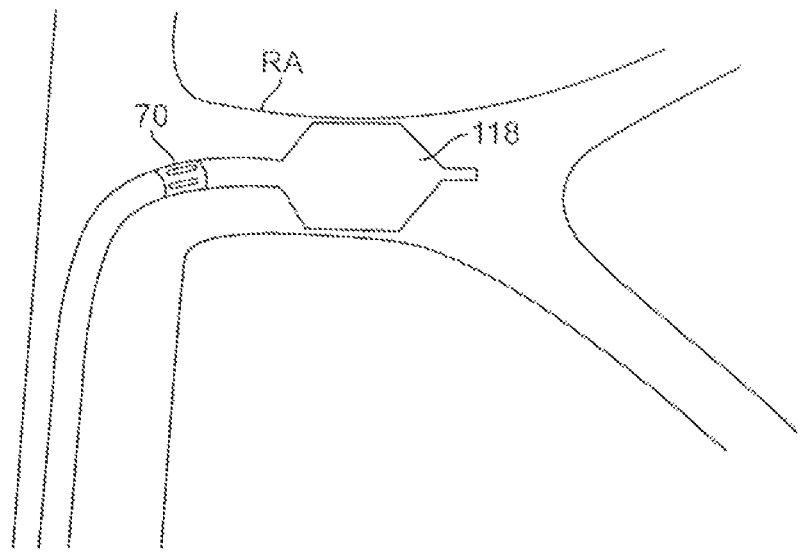
FIGS. 8A-8C provide example applications of pressure measurement devices in accordance with one embodiment of the technology disclosed herein.
Figure 8B:
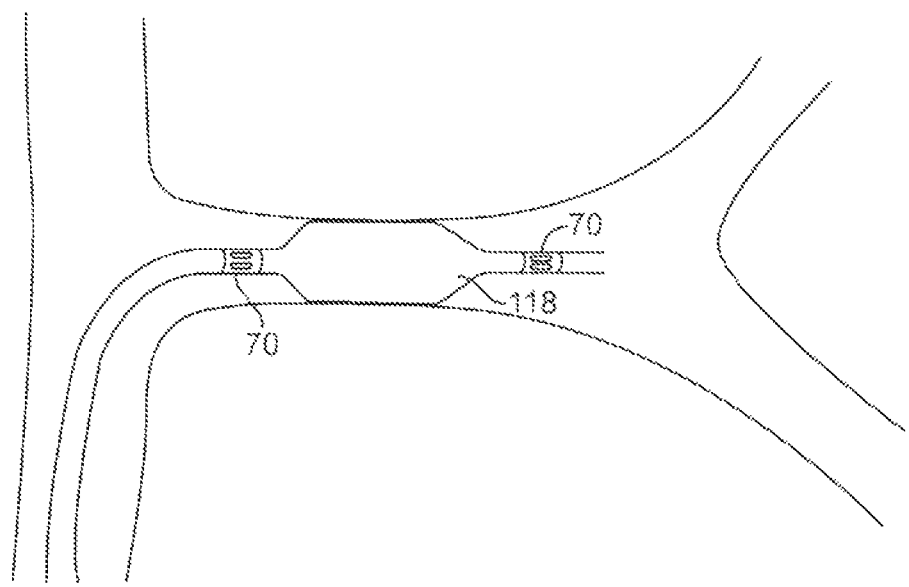
Figure 8C:
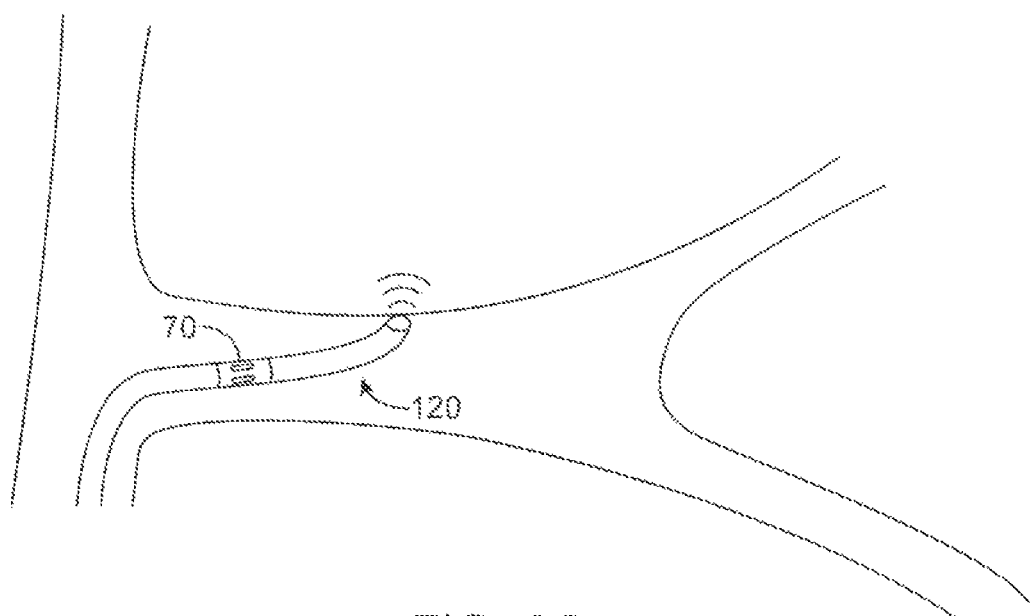

FIGS. 8A-8C provide examples of the applications of pressure measurement devices 70 in situ. FIG. 8A illustrates an example wherein a balloon 118 is located in renal artery RA and a pressure measurement device 70 is provided to measure blood pressure in the renal artery RA. Balloon 118 could be, for example a balloon for neuromodulation such as a cryo-ablation balloon, a balloon with RF electrodes to deliver RF energy to the tissue, or other balloon configured for neuromodulation.

FIG. 8B illustrates an example in which two pressure measurement devices 70 are provided, one at each end of balloon 118 inflated in the renal artery RA. The pressure measurement devices 70 measure the blood pressure at each end of the balloon 118. The measurement of a significantly lower blood pressure on the distal side of balloon 118 indicates a good occlusion. FIG. 8C illustrates an example in which pressure measurement device 70 is incorporated into an RF ablation device to measure blood pressure during and immediately after a renal neuromodulation procedure in the renal artery RA. As these examples serve to illustrate, there are number of applications for one or more pressure measurement devices to be provided at or proximal to therapeutic assembly 21.

In other embodiments, one or more pressure measurement devices 70 can be collocated with one or more electrodes (or other delivery devices) used to deliver RF energy to the renal nerves. Consider an example where one or more electrodes are disposed on a catheter for placement against the target tissue. The one or more electrodes can be positioned on a catheter tip for delivery to the treatment site. In other embodiments, one or more electrodes can be positioned on a shape-set delivery device (e.g., NiTi wire) that, when expanded, takes its shape to be positioned against the artery wall. As still a further example, the shape set delivery device on which one or more electrodes are mounted can be a helical support structure 22, such as that described above in FIGS. 3 and 4. In other embodiments, one or more electrodes can be mounted on other structures for placement against the targeted tissue.

In the case of RF renal neuromodulation, electrode positioning is intended to cause the one or more electrodes to come into sufficient contact with the artery wall such that RF energy can be appropriately delivered to the renal nerves. However, it can be difficult to determine whether the support structure 22 is properly expanded and whether sufficient contact is made by the support structure 22 (and hence the electrodes 24) with the artery wall. Accordingly, one or more pressure measurement devices 70 can be disposed on the catheter (or on support structure 22) and used to detect or measure correct apposition of the renal neuromodulation electrodes.

Figure 9:
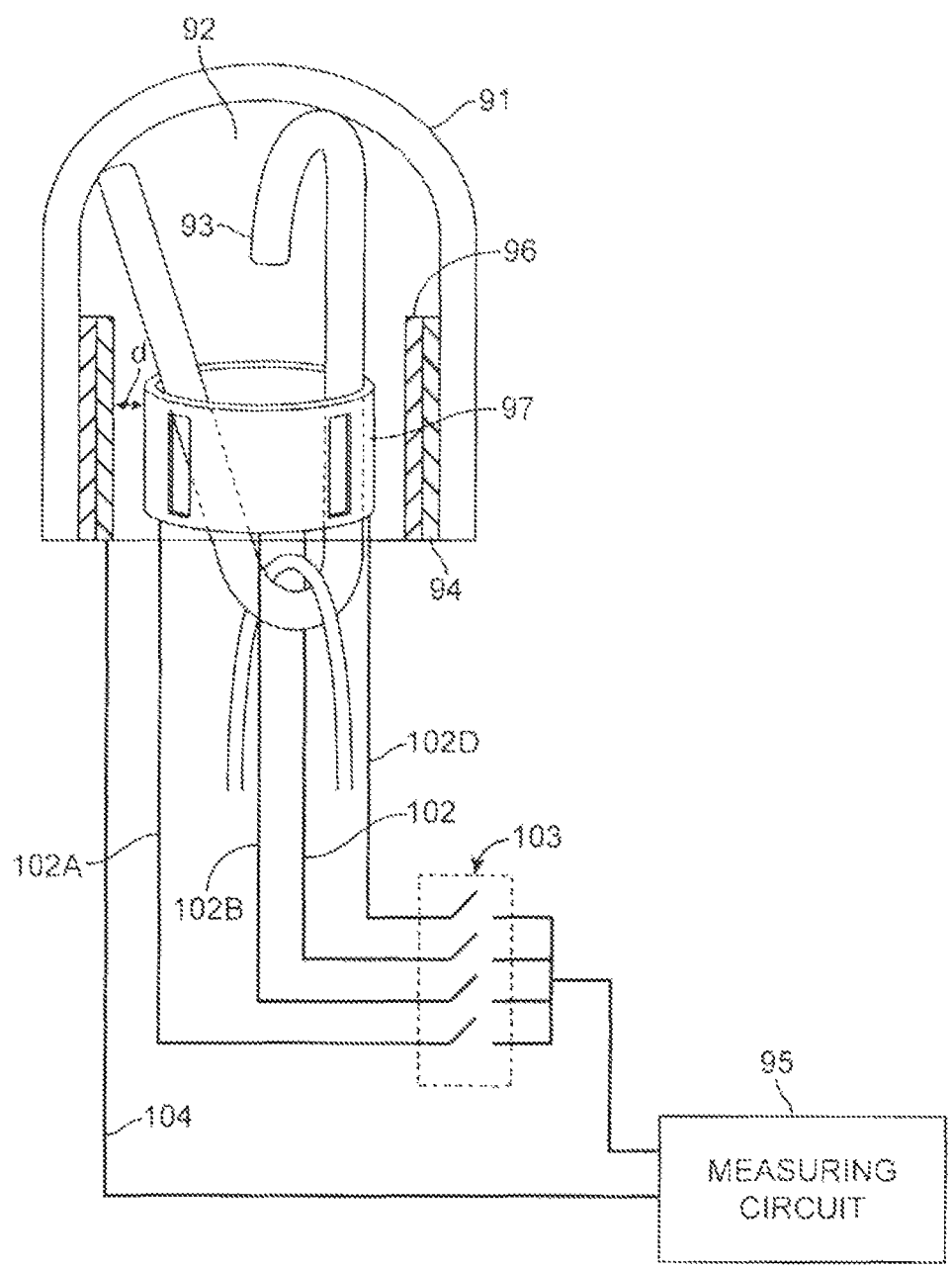
FIG. 9 is a diagram illustrating an example of a pressure sensor integrated within an electrode in accordance with one embodiment of the technology described herein.

FIG. 9 is a diagram illustrating an example of a pressure sensor integrated within an electrode in accordance with one embodiment of the technology described herein. Referring now to FIG. 9, an electrode 24 has a conductive outer surface 91 and a hollow inner body region. Contact 93 is electrically connected to energy source or console 26 and couples the RF energy (in the case of RF neuromodulation) to electrode 24. A layer of insulation 94 is provided about the inner circumference or perimeter of electrode 24. The pressure sensor elements are disposed within the layer of insulation 94 to electrically isolate the pressure sensor elements from the electrode body.

In the illustrated example, a multi-region, annular capacitive sensor is used as the pressure sensor. An outer conductive surface 96 surrounds an inner conductive surface 97 with a gap between the two conductive surfaces 96, 97. Inner conductive surface 97 is slotted or otherwise separated to create different conductive regions about the inner conductive surface 97. Similar to the embodiment shown in FIGS. 5 and 6A, inner and outer conductive surfaces 96, 97 can be made of cylindrical conductors disposed in coaxial relation to one another. Unlike the embodiment shown in FIGS. 5 and 6A, inner conductive surface 97 is slotted and outer conductive surface 96 forms a continuous cylindrical conductor, however this configuration can be reversed. The slots divide conductive surface 97 into a plurality of regions. The example of FIG. 9 includes four regions, but only three are visible in the drawing.

Four conductive paths 102A, 102B, 102C and 102D each electrically connecting its respective region of the inner conductive surface 97. Switches 103 are provided to selectively switch one of the four capacitive elements to measuring circuit 95. Switches can be manually actuated or they can be controlled by algorithms (e.g., by evaluation/feedback algorithms 30) to select which capacitive element is being measured. In another embodiment, multiple measuring circuits can be provided to allow simultaneous measurement of capacitive elements without the need for switching.

In various embodiments, outer conductive surface 96 can be continuous so that only one lead 104 is needed from surface 96 to measure the capacitances of the regions. In other embodiments, outer conductive surface 96 can be segmented into different sections or regions corresponding to the regions of inner conductive surface 97.

FIG. 10A is a diagram illustrating an example of a pre-shaped support structure 22 with a plurality of energy delivery elements 24. Support structure 22 can be, for example, a catheter tip, a shape set wire (e.g., shape set in a helical or other geometry), or other structure used to place and/or support energy delivery elements 24. For clarity of illustration, support structure 22 is illustrated in an elongated configuration, however, it will be understood by those of ordinary skill in the art upon reading this description that when expanded, support structure 22 can take on a desired shape (e.g., a helical shape) to cause the electrodes 24 to contact the arterial walls. For example, support structure 22 can be implemented using a helical structure as described above with reference to FIGS. 3 and 4.

Because the feedback provided through over-the-wire and guide-wire catheters (e.g., via feel or fluoroscopy) is generally not sufficient to inform the clinician whether good and proper contact of the electrodes is made with the arterial wall, additional feedback mechanisms can be beneficial. Likewise, because in some embodiments the electrodes may be disposed on one side of the support structure 22, knowledge of the orientation of the expanded support structure 22 can be important. Accordingly, in various embodiments, one or more pressure measurement devices 70 can be disposed on the support structure 22 proximal to the electrodes 24 to provide position sensing of the support structure 22 and hence the electrodes 24.

FIG. 10B is a diagram illustrating an example in which a plurality of pressure measurement devices 70 are disposed on support structure 22 proximal to a plurality of electrodes 24. In the example illustrated in FIG. 10B, pressure measurement devices 70 are disposed between adjacent electrodes 24. Where capacitive pressure measurement devices 70 are used, the pressure measurement devices 70 are electrically insulated from the arterial wall via sheath 132. Sheath 132 is provided to prohibit the arterial wall from affecting the capacitance of pressure measurement devices 70. Additionally, control wires (not shown) are included to provide the RF signals necessary to stimulate electrodes 24, and sense wires (not shown) are included to electrically connect the conductive surfaces of pressure measurement devices 70 to the measuring circuit (e.g., wires 82 in the embodiment illustrated in FIG. 6A). In other embodiments, pressure measurement devices 70 include measuring circuitry and wireless transmitters to transmit pressure measurements to the monitoring system.

The example illustrated in FIG. 10B includes a plurality of electrodes 24 distributed along the illustrated section of support structure 22. This example further shows pressure measurement devices 70 disposed between each adjacent pair of electrodes 24. In various embodiments, one or more pressure measurement devices 70 is disposed adjacent to or within (e.g., FIG. 9) an electrode 24. Placing one or more pressure measurement devices 70 closely adjacent an electrode 24 allows the pressure measurement devices 70 to be used to sense the position and orientation of the electrode while reducing or eliminating effects of any torsion in support structure 24. Although the example in FIG. 10B shows electrodes and pressure measurement devices 70 closely spaced along the entire length of the segment, other spacings can be used. For example, an electrode and one or more adjacent pressure measurement devices 70 can be spaced about a helical support structure 22 quarter-turn intervals, half-turn intervals, full-turn intervals, or at other spacing intervals.

The example of FIG. 10B is now described in terms of the example pressure measurement device illustrated in FIGS. 5 and 6A. Capacitive pressure measurement device 70, as described above in FIGS. 5 and 6A, can be divided into a plurality of regions about the device. Accordingly, the capacitance of, and hence the pressure applied to, each region of the device can be measured separately. By measuring the capacitance of a given region, the relative capacitances between regions, or changes in capacitance of one or more regions, the monitoring system (e.g., by evaluation/feedback algorithms 30) can determine whether pressure is being applied to a particular region of a particular pressure measurement device 70. During deployment and placement in the vasculature, increased pressure above a nominal pressure in a particular region of a pressure measurement device 70 may indicate that particular region of the device is contacting the vessel wall. A measurement of the change in capacitance above nominal, or the absolute capacitance, can give an indication of the amount of pressure being applied against the vessel wall. Likewise, a sense in increased pressure of a first region over that of other regions of the device can indicate that the first region is contacting the vessel wall.

Figure 11:
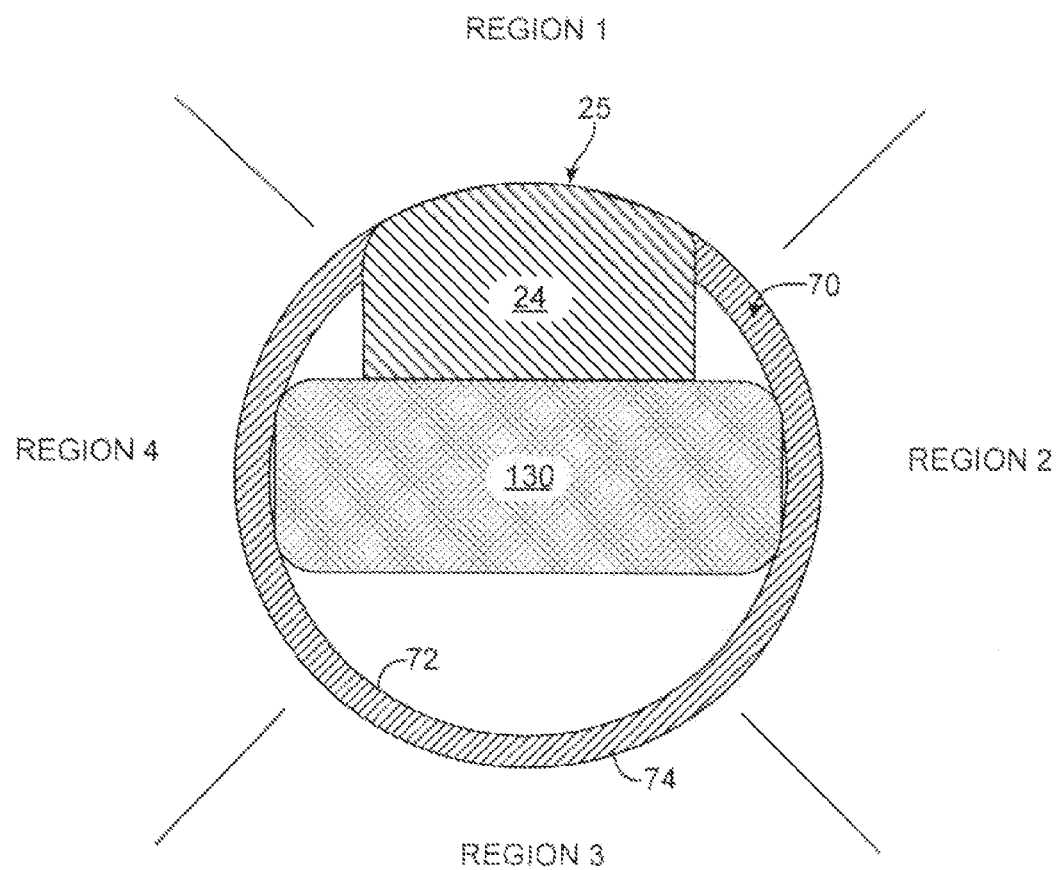
FIG. 11 provides a cross-sectional view of a pressure measurement device mounted circumferentially about a support structure in accordance with one embodiment of the technology disclosed herein.

Consider the example of FIG. 11, which is a cross-sectional view showing a pressure measurement device 70 mounted circumferentially about a pre-shaped wire 130. In this example, an electrode 24 is disposed on a surface of wire 130. Also in this example, there are four slots 75 (not shown) in the outer surface 74 of pressure measurement device 70, effectively dividing the pressure measurement device 70 into four regions. These four regions are labeled Region 1, Region 2, Region 3 and Region 4. Accordingly, pressure measurement device 70 effectively includes 4 capacitive elements, one corresponding to each region, whose capacitances can be separately measured to detect the pressure applied, if any, in each region.

In an example application of this configuration, it would be desired that the support structure 22 be positioned such that the outer surface 25 of the electrode 24 is put into contact with the vessel wall. Accordingly, during placement of the device in preparation for the procedure, the system is configured to look for sufficient pressure in Region 1 to indicate that surface 25 of electrode 24 is in proper contact with the vessel wall. As such, a monitoring system (e.g., by evaluation/feedback algorithms 30) can be used to detect the appropriate pressure in Region 1 and to alert the clinician when proper placement is attained. Audible, visual, or haptic feedback can be used to provide the desired alert indicating proper placement.

Likewise, the monitoring system can also be used to detect whether one of the other regions (e.g., Region 2, Region 3, or Region 4) is contacting the vessel wall. If pressure measurements indicate that one or more of the other regions is contacting the vessel wall instead of Region 1, the monitoring system can provide an indication to the clinician that contact is made but alignment or orientation is off. The system can further be configured to indicate to the clinician which region is making contact so the clinician can determine what adjustments may be necessary to achieve proper contact of electrode 24. For example, if the system determines that contact is being made with Region 4, the system can alert the user that Region 4 is contacting the vessel wall and can instruct the user to rotate the orientation of the structure by 90 degrees counterclockwise. As this illustrates, pressure measurements of the various regions of a pressure sensor can be used to determine electrode positioning and orientation. Particularly, the measurements can indicate whether the desired surface 25 is contacting the vessel wall and whether the electrode 24 is lying flat against the tissue. The measurements can also indicate whether the electrode 24 is positioned on its edge or is otherwise not properly oriented. Because the pressure measurements can be used to determine orientation of the support structure 22 and electrode 24 relative to the vessel wall, a visual display can be provided showing the clinician the orientation of the device on a display screen (e.g., display 33). With this visual information, the clinician can determine how to adjust orientation of the device to achieve proper contact.

In the case of embodiments using multiple pressure measurement devices 70, similar positioning feedback mechanisms can be used for each of the multiple devices. Accordingly, with such embodiments, the clinician can determine existence and quality of physical contact of the electrode with the targeted tissue.

Also, because there are multiple regions, a pressure measurement device 70 configured in this fashion can be used to sense placement of the desired region against the vessel wall, and to sense patient blood pressure via one or more of the other regions. Accordingly, simultaneous or sequential measurements can be used to determine placement and to measure patient blood pressure with a measurement device 70.

In some embodiments, impedance sensors are used in conjunction with pressure sensors to provide positioning feedback. Because the impedance of blood is different from that of tissue, impedance measured at an electrode will rise when it makes contact with tissue. Accordingly, impedance can be used to measure contact by measuring the rise in impedance as an electrode goes from the blood pool to tissue. However the value of the rise in impedance can vary based on factors such as tissue type, patient anatomy, varied blood flow, etc. Thus, it is difficult to choose a threshold to universally use across patients to determine contact with impedance alone. Accordingly, in some embodiments, impedance and pressure sensors are used to provide positioning feedback relative to tissue. This is now described in the context of a simple example. Consider an example of a helical support structure that can be expanded to contact the vessel wall. When the device is positioned in the artery, but before it is expanded or deployed such that the electrodes are not making contact with tissue, reference impedance and pressure measurements are made and the result recorded. As the helical structure is being expanded, pressure is monitored. When the pressure sensor indicates an increase in pressure, this signals contact of the support structure. Depending on the proximity of the pressure sensors to the electrodes, this could also provide some indication of contact by the electrode. However, because the pressure sensors are adjacent the electrodes and they do not occupy the same space, contact by a sensor is not a guarantee that there is contact by the electrode. Therefore, electrode contact can be confirmed by impedance measurements. Particularly, impedance can also be checked and compared against the reference impedance measurement. A change in impedance (e.g., a rise) in impedance (which can be measured, for example, by measuring the current at the return) gives an indication that the electrode itself is making contact. Accordingly, using both impedance and pressure measurements can provide additional information to the clinician about the electrode contact.

Figure 12:
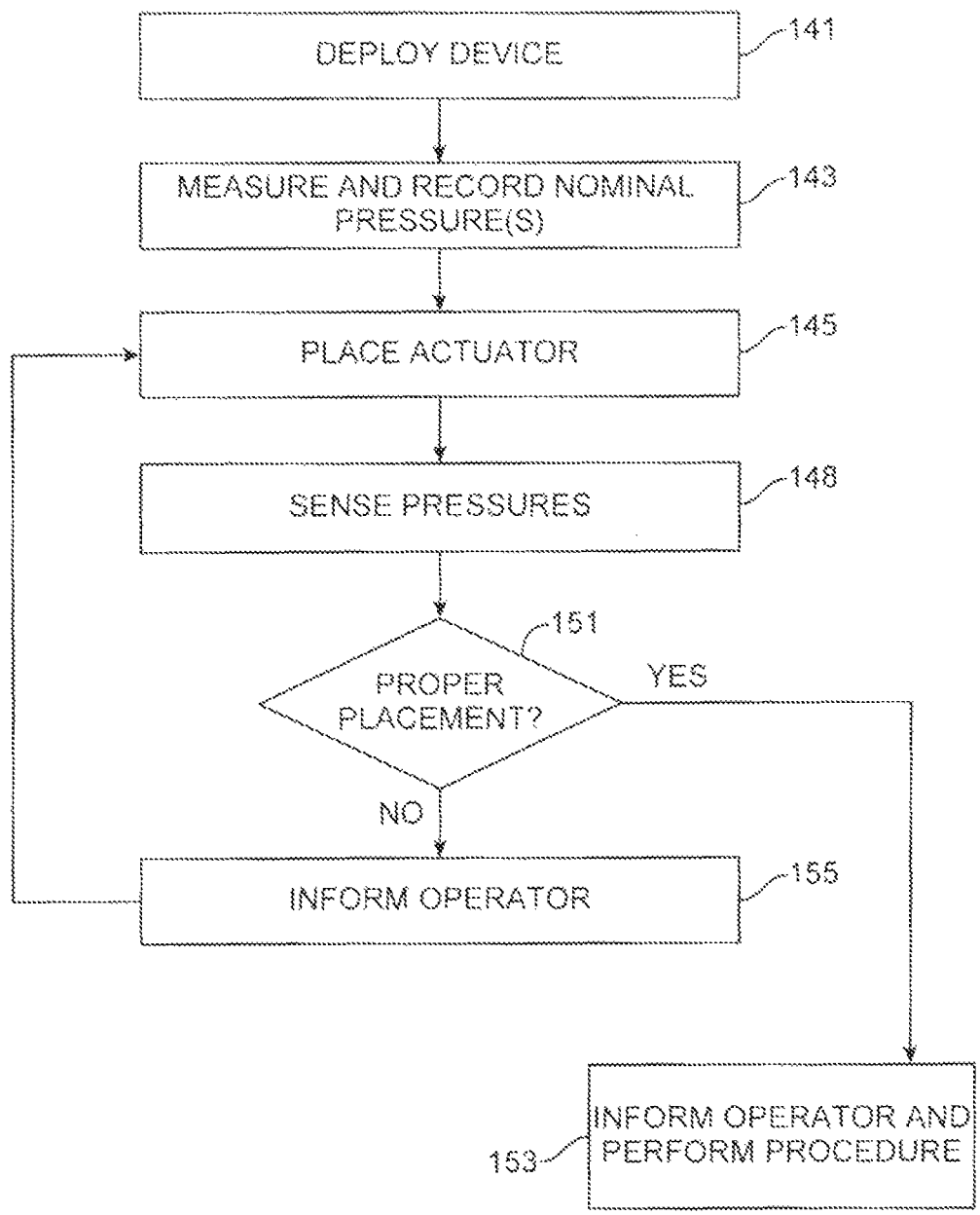
FIG. 12 is an operational flow diagram illustrating an example process for using a pressure sensor to determine placement in accordance with one embodiment of the technology disclosed herein.

FIG. 12 is an operational flow diagram illustrating an example process for using a pressure sensor to determine placement in accordance with one embodiment of the technology described herein. Referring now to FIG. 12, at operation 141 the treatment device is deployed. For example, in the case of RF ablation for renal neuromodulation, the devices deployed with one or more electrodes positioned at the catheter tip to provide RF energy for renal neuromodulation. In accordance with various embodiments, one or more pressure sensors are included adjacent to the RF electrodes to allow position sensing. One example configuration for this is that illustrated above with reference to FIG. 10B.

At operation 143, the nominal pressures of the pressure sensors in the bloodstream near the treatment site are measured and recorded. This can be used to provide a reference pressure measurement for the one or more pressure sensors included with the device. In some embodiments, impedance measurements can also be made at this time to determine a reference impedance measurement prior to deployment. At operation 145, the actuator is placed at the treatment site. For example, the pre-shaped wire can be deployed to position the electrodes against the vessel wall.

At operation 148, the pressures of the one or more pressure sensors are measured. This step can be performed continuously during placement of the actuator, or can be performed at periodic intervals to check placement. The goal of this step is to measure pressures to determine whether or not placement against the vessel wall has been achieved. For example, as described above with reference to FIG. 11, measurement of the pressures at various regions of one or more pressure sensing devices can be used to determine an orientation of the pressure sensing device as it is placed into contact with the vessel wall.

If pressure sensing determines a proper placement (e.g., proper orientation) has been achieved, the operator is informed and the procedure can commence. This is illustrated at operations 151 and 153. For example, a multi-region pressure sensor such as that described above with reference to FIG. 11 can be used to determine orientation of the assembly. If, on the other hand, pressure sensing operation indicates that proper placement has not been achieved, the operator is informed and the placement is adjusted in an attempt to achieve proper placement. This is illustrated at operations 151 and 155. In some embodiments, impedance measurements can also be made and compared against the reference impedance measurement to determine whether a change in impedance indicates contact. Likewise, impedance measurements can also be made during the treatment process to determine whether changes in impedance indicate the formation of lesions.

Figure 13:
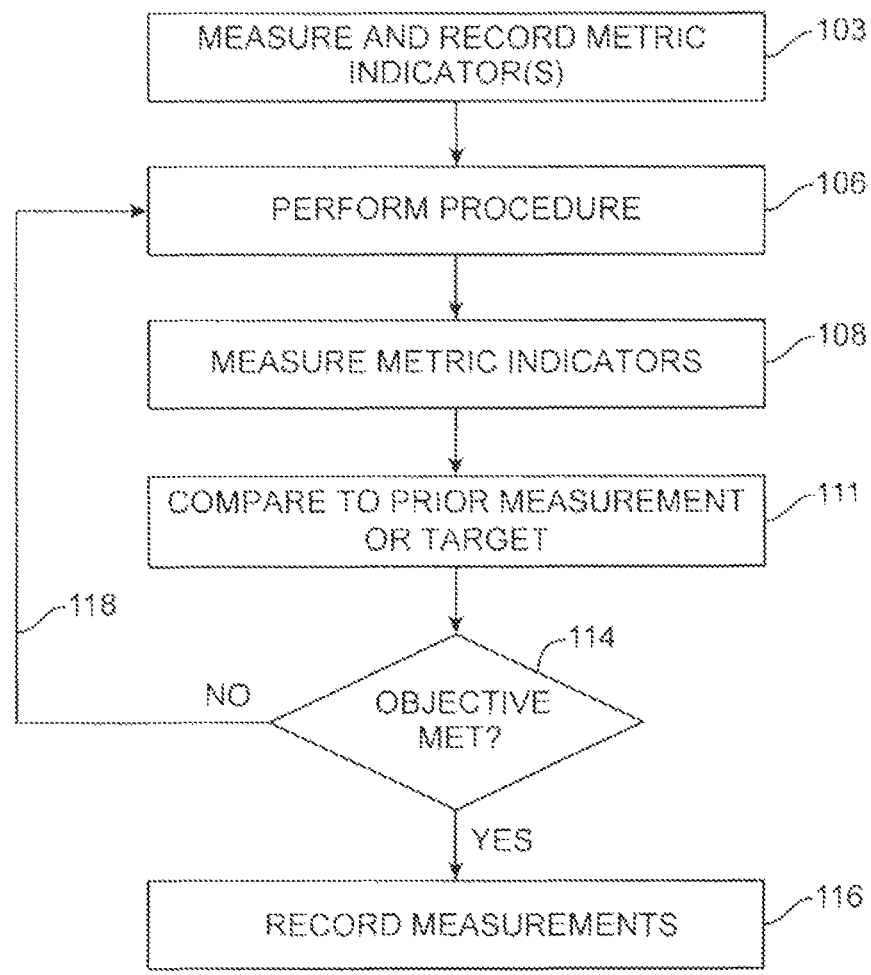
FIG. 13 is a diagram illustrating an example process for using feedback to determine the effectiveness of treatment in accordance with one embodiment of the systems and methods described herein.

Feedback can be used for purposes other than apposition judgment. In some embodiments, feedback is used to determine the effectiveness of renal neuromodulation treatment. For example, in the case of renal neuromodulation, one or more various patient metrics can be measured and used to determine the efficacy of the ablation and/or the effectiveness of applied treatment. FIG. 13 is a diagram illustrating an example process for using feedback to determine the effectiveness of treatment in accordance with one embodiment of the systems and methods described herein. Referring now to FIG. 13, at operation 103 one or more patient metrics are measured and recorded. For example, metrics such as patient blood pressure and norepinephrine levels can be measured. Other metrics indicating whether a lesion was successfully formed can include tissue temperature, impedance, and blood flow.

In further embodiments, blood flow can be monitored in real time and the flow rate information used to inform the process. For example, blood flow can be calculated using pressure measurements from a plurality of sensors separated from one another by known distances and positioned along the axial length of the artery. The system can be configured to measure pressure changes across the plurality of sensors and detect the times at which such changes occur. For example, the time at which a measured rise in pressure occurs at one sensor is compared to the time at which a corresponding rise in pressure occurs at another sensor, and a time difference calculated. The blood flow rate can then be determined by dividing the known distance between those two sensors by the calculated time difference.

Blood flow can have a significant effect on electrode temperature and the ability to deliver RF energy at certain power levels before damaging the artery wall. In addition, blood flow could be an indication that the vessel is constricting and lesions are being formed. Accordingly, the power delivery algorithm can be configured to measure blood flow rates and adjust power levels accordingly. For example, in high-blood-flow conditions, power can be increased to account for increased cooling provided by the higher flow rate. Likewise, in low-blood-flow conditions, power can be reduced. The process for measuring blood flow rates could include, for example, taking an initial blood-flow measurement to establish a reference. With the reference established, periodic measurements can be taken throughout the procedure and compared to the reference to monitor changes. The system can be configured to alert the clinician where the changes exceed a predetermined threshold, in response to which the procedure may be terminated. In another embodiment, the procedure can be performed (e.g., for a predetermined time) and blood-flow measurements taken before or after a procedure could be used to give the clinician a possible indication of treatment efficacy. It is noted that an increased rate of blood flow could be an indication that a vessel is constricting due to the formation of lesions.

At operation 106, the procedure is performed. For example, in one embodiment the procedure can be a renal neuromodulation procedure performed using a system such as, for example, system 1 illustrated in FIG. 1. Although the procedure performed with the example method of FIG. 13 can be any of a number of different procedures, the process is described herein in terms of a renal neuromodulation procedure. Description in these terms is provided for ease of discussion only, and after reading this description, one of ordinary skill in the art will understand how the systems and methods described herein can be implemented with any of a number of different medical procedures. Examples of such medical procedures include, without limitation denervation or neuromodulation of non-renal targets or ablations of various anatomical elements.

At operation 108, the patient metrics are again measured. This subsequent measurement can be performed at one or more intervals throughout the procedure, and it can be performed at the conclusion of the procedure. Preferably, the patient metrics measured at operation 108 during and after the procedure are the same metrics measured before the procedure at operation 103.

At operation 111, the measurement or measurements made at operation 108 are compared with the corresponding measurement(s) made at operation 108 to determine the efficacy of the treatment. For example, in the case of renal neuromodulation, one metric for determining the effectiveness of the treatment is the patient's systolic blood pressure. This is because in people with hypertension, the renal nerves are hyperactive, which raises blood pressure. Denervation of the renal sympathetic nerve can result in a large and highly significant reduction in systolic blood pressure.

If the desired level of change in the one or more metrics is met, the efficacy of the treatment is verified, the treatment can be concluded, and the final measurements can be recorded. This is illustrated by operations 114 and 116. On the other hand, if the desired level of change in the one or more metrics is not met, the clinician may determine to continue the procedure as illustrated by flow line 118. Continuing with the above example, in the case of renal neuromodulation, if the measurement shows the desired level of reduction in the patient's blood pressure, the treatment can be suspended. If the desired level of reduction is not met, the procedure may be continued. It is noted that immediate reductions in blood pressure do not always accompany a successful renal neuromodulation procedure.

In the above-described example, measurements made during or post-procedure are compared with prior measurements to determine whether the desired level of change in condition has been achieved. In other embodiments, measurements are made to determine whether a predetermined target or objective has been met. For example, in the case of treating hypertension using renal neuromodulation, blood pressure measurements made during or post-procedure can be evaluated against a target blood pressure level to determine the efficacy of the treatment in real time.

In some embodiments, the measurements can be made continuously or at periodic or other intervals and evaluation/feedback algorithms 31 can be used to determine the results. Audible alerts, display cues, haptic feedback or other techniques can be used to alert the physician, health-care worker or other clinician when the desired treatment goals have been achieved. For example, the system can be configured to sound a chime or other audible alert when the desired blood-pressure level is met, or to cause handle 34 to gently vibrate. Likewise, the system can be configured to display the blood pressure on screen 33 for visual feedback of actual measurements.

Figure 14:
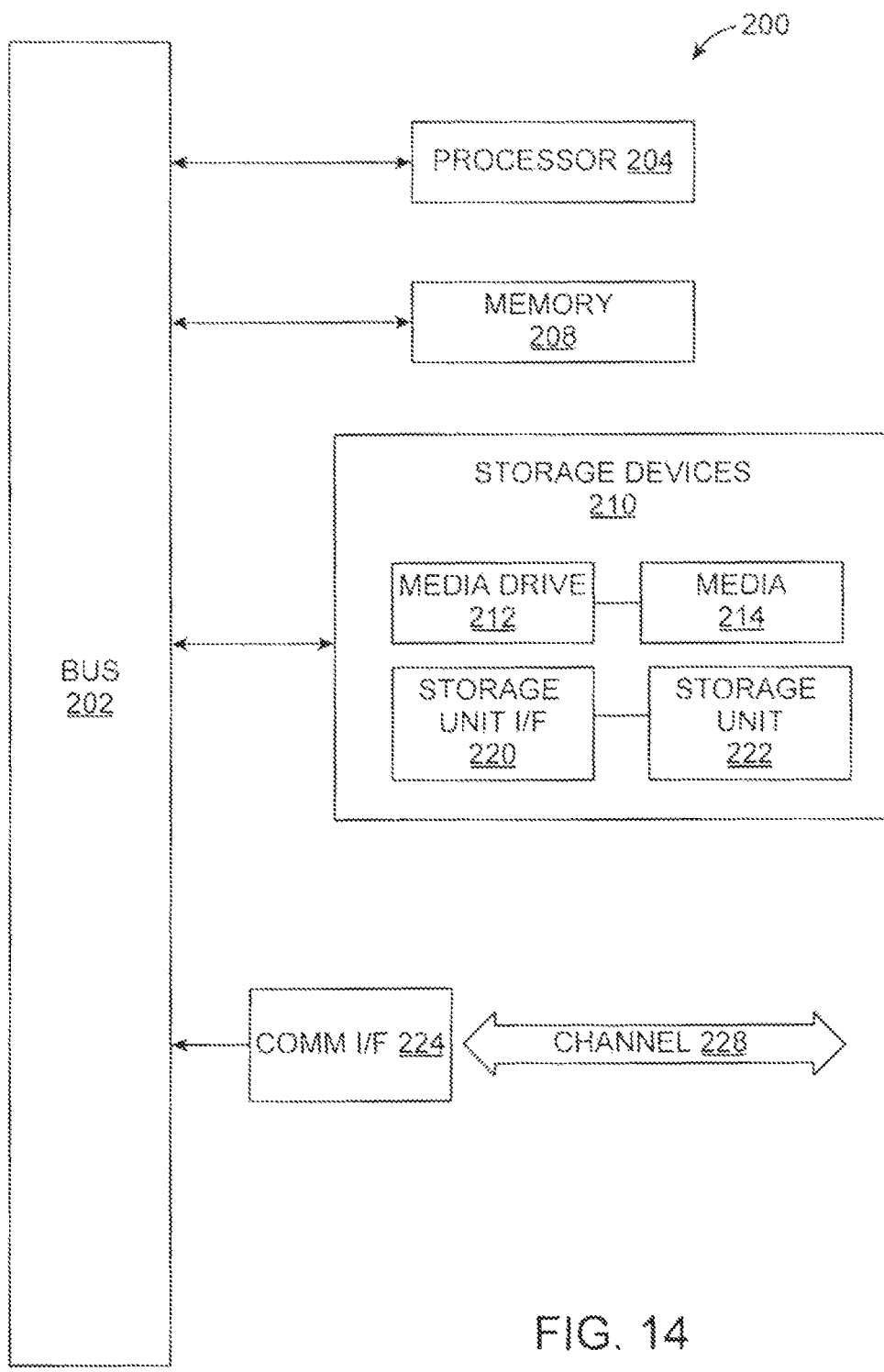
FIG. 14 illustrates an example computing module that may be used in implementing various features of embodiments of the systems and methods disclosed herein.

Although the above examples are described in terms of the pressure measurement device 70 illustrated in FIG. 5, the system is not limited for use with this device. Indeed, other pressure measurement devices can be used including, for example, microelectromechanical systems (MEMS) devices and other pressure sensors. One example of a MEMS device that is suitable for use as a pressure sensor with the systems and methods disclosed herein are wireless pressure sensors provided by CardioMEMs, Inc., located at 387 Technology Circle NW in Atlanta, Ga. 30313. Also, although some examples set forth above describe mounting one or more electrodes and sensors on a pre-shaped core, one of ordinary skill in the art after reading this description will appreciate that other delivery mechanisms or applicators can be used with the technology described herein. Likewise, although the actuator is described in various examples as an RF electrode, one of ordinary skill in the art after reading this description will appreciate that the technology described herein can be used to facilitate the positioning of other actuators, such as temperature probes, heat- or cryo-tips, ulstrasonic transducers, and so on.

Where components or modules of the invention are implemented in whole or in part using software, in one embodiment, these software elements can be implemented to operate with a computing or processing module capable of carrying out the functionality described with respect thereto. One example of a computing module is shown in FIG. 14. Various embodiments are described in terms of this example-computing module 200. After reading this description, it will become apparent to a person skilled in the relevant art how to implement the invention using other computing modules or architectures.

Referring now to FIG. 14, computing module 200 may represent, for example, computing or processing capabilities found within desktop, laptop and notebook computers; hand-held computing devices (PDA's, smart phones, tablets, cell phones, palmtops, etc.); mainframes, supercomputers, workstations or servers; or any other type of special-purpose or general-purpose computing devices as may be desirable or appropriate for a given application or environment. Computing module 200 might also represent computing capabilities embedded within or otherwise available to a given device.

Computing module 200 might include, for example, one or more processors, controllers, control modules, or other processing devices, such as a processor 204. Processor 204 might be implemented using a general-purpose or special-purpose processing engine such as, for example, a microprocessor, controller, or other control logic. In the illustrated example, processor 204 is connected to a bus 202, although any communication medium can be used to facilitate interaction with other components of computing module 200 or to communicate externally.

Computing module 200 might also include one or more memory modules, simply referred to herein as main memory 208. For example, preferably random access memory (RAM) or other dynamic memory, might be used for storing information and instructions to be executed by processor 204. Main memory 208 might also be used for storing temporary variables or other intermediate information during execution of instructions to be executed by processor 204. Computing module 200 might likewise include a read only memory ("ROM") or other static storage device coupled to bus 202 for storing static information and instructions for processor 204.

The computing module 200 might also include one or more various forms of information storage mechanism 210, which might include, for example, a media drive 212 and a storage unit interface 220. The media drive 212 might include a drive or other mechanism to support fixed or removable storage media 214. For example, a hard disk drive, a floppy disk drive, a magnetic tape drive, an optical disk drive, a CD or DVD drive (R or RW), or other removable or fixed media drive might be provided. Accordingly, storage media 214 might include, for example, a hard disk, a floppy disk, magnetic tape, cartridge, optical disk, a CD or DVD, or other fixed or removable medium that is read by, written to or accessed by media drive 212. As these examples illustrate, the storage media 214 can include a computer usable storage medium having stored therein computer software or data.

In alternative embodiments, information storage mechanism 210 might include other similar instrumentalities for allowing computer programs or other instructions or data to be loaded into computing module 200. Such instrumentalities might include, for example, a fixed or removable storage unit 222 and an interface 220. Examples of such storage units 222 and interfaces 220 can include a program cartridge and cartridge interface, a removable memory (for example, a flash memory or other removable memory module) and memory slot, a PCMCIA slot and card, and other fixed or removable storage units 222 and interfaces 220 that allow software and data to be transferred from the storage unit 222 to computing module 200.

Computing module 200 might also include a communications interface 224. Communications interface 224 might be used to allow software and data to be transferred between computing module 200 and external devices. Examples of communications interface 224 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 224 might typically be carried on signals, which can be electronic, electromagnetic (which includes optical) or other signals capable of being exchanged by a given communications interface 224. These signals might be provided to communications interface 224 via a channel 228. This channel 228 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, main memory 208, storage unit interface 220, storage media 214, and channel 228. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 200 to perform features or functions of the present disclosure as discussed herein.

III. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal neuromodulation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 15:
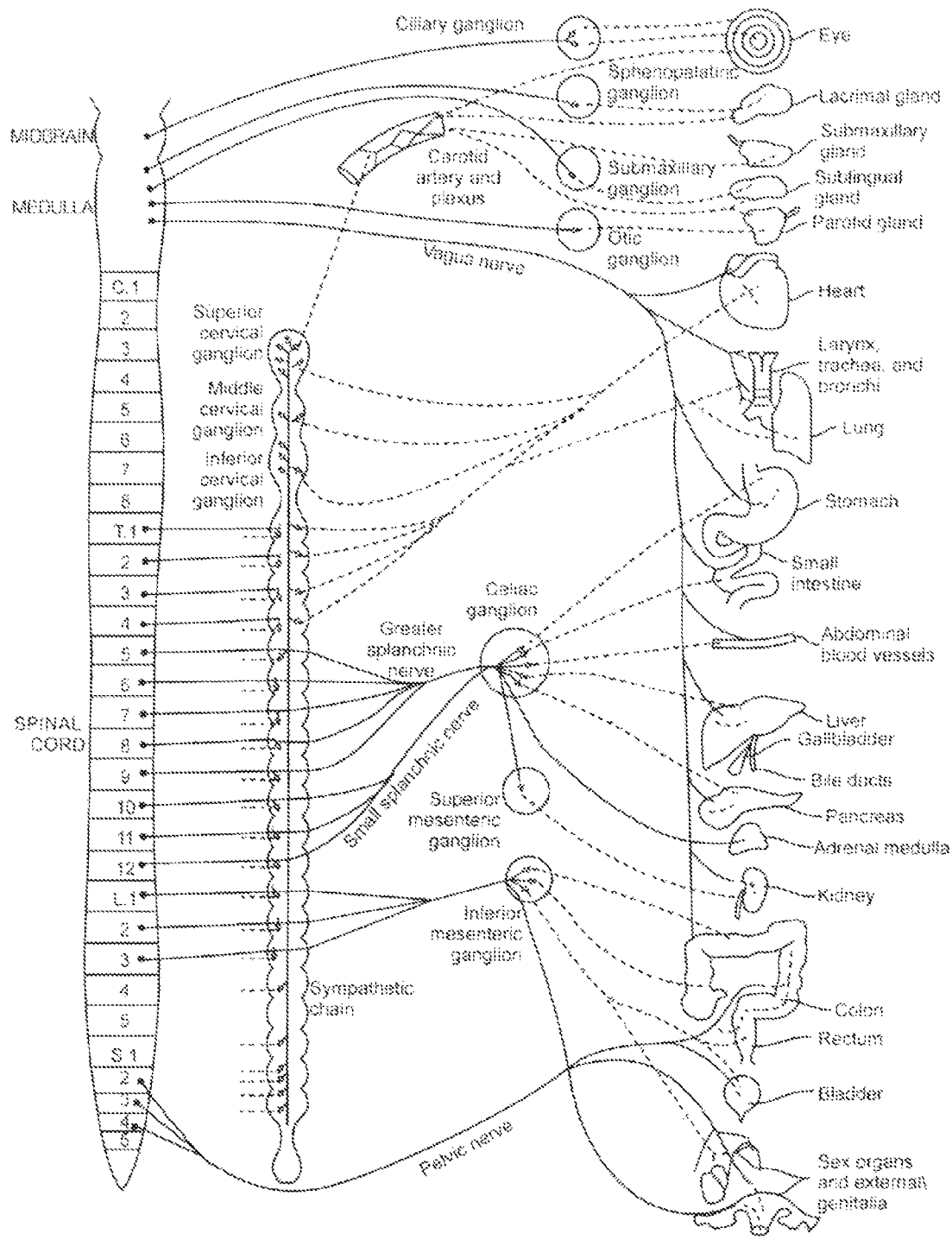
FIG. 15, illustrates a network of nerves that make up the sympathetic nervous system, allowing the brain to communicate with the body.

As shown in FIG. 15, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 16:
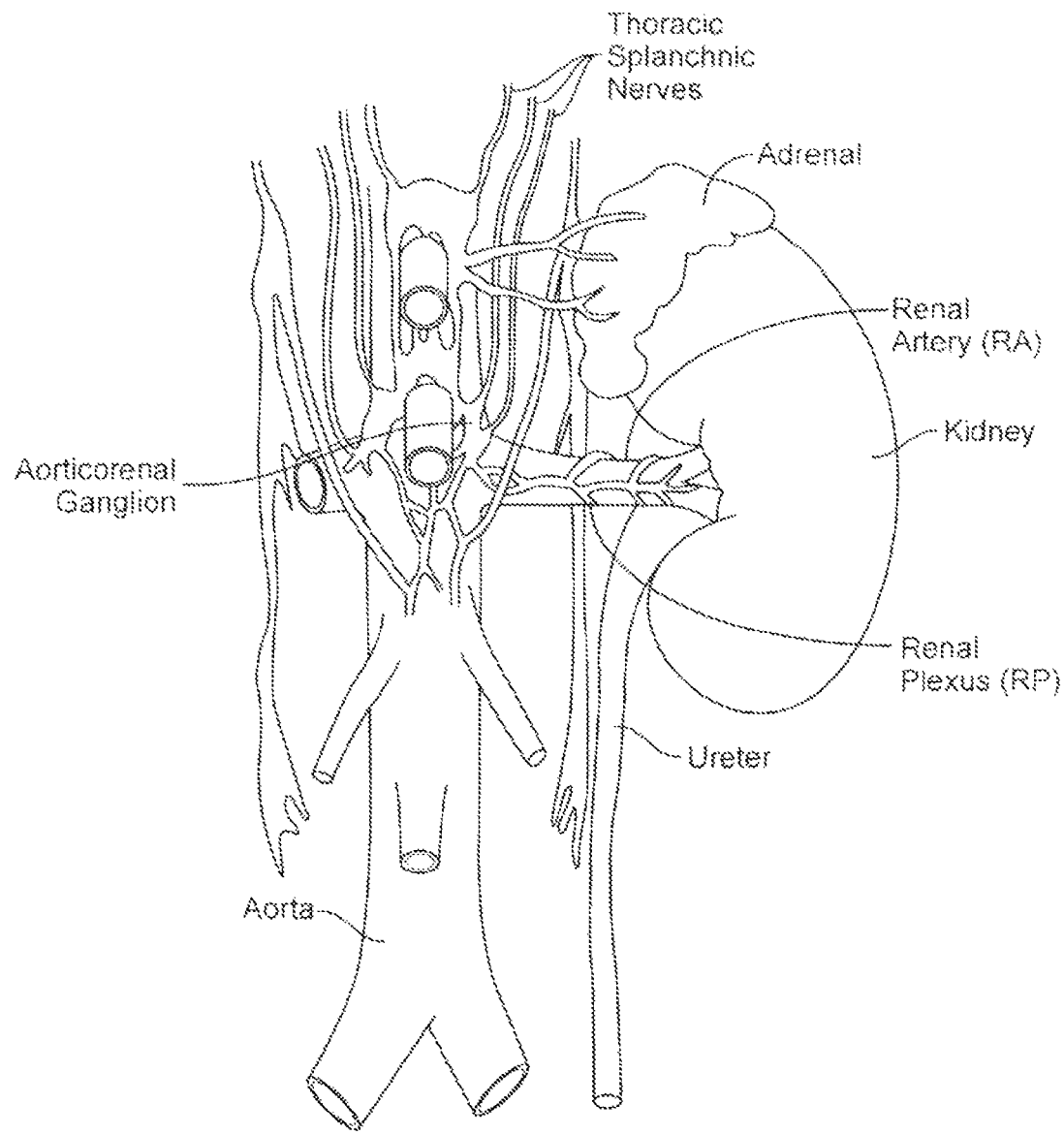
FIG. 16, illustrates the kidney, innervated by the renal plexus (RP), which is intimately associated with the renal artery.

As shown in FIG. 16, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing overactivity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

i. Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

ii. Renal Sensory Afferent Nerve Activity

Figure 17A:
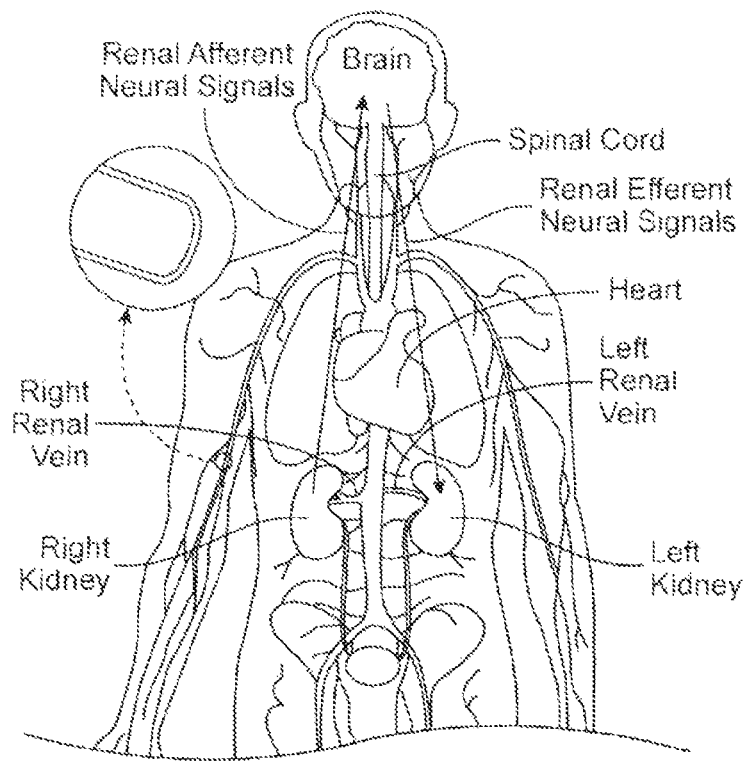
FIGS. 17A and 17B, illustrate afferent communication from the kidney to the brain and from one kidney to the other kidney (via the central nervous system).
Figure 17B:
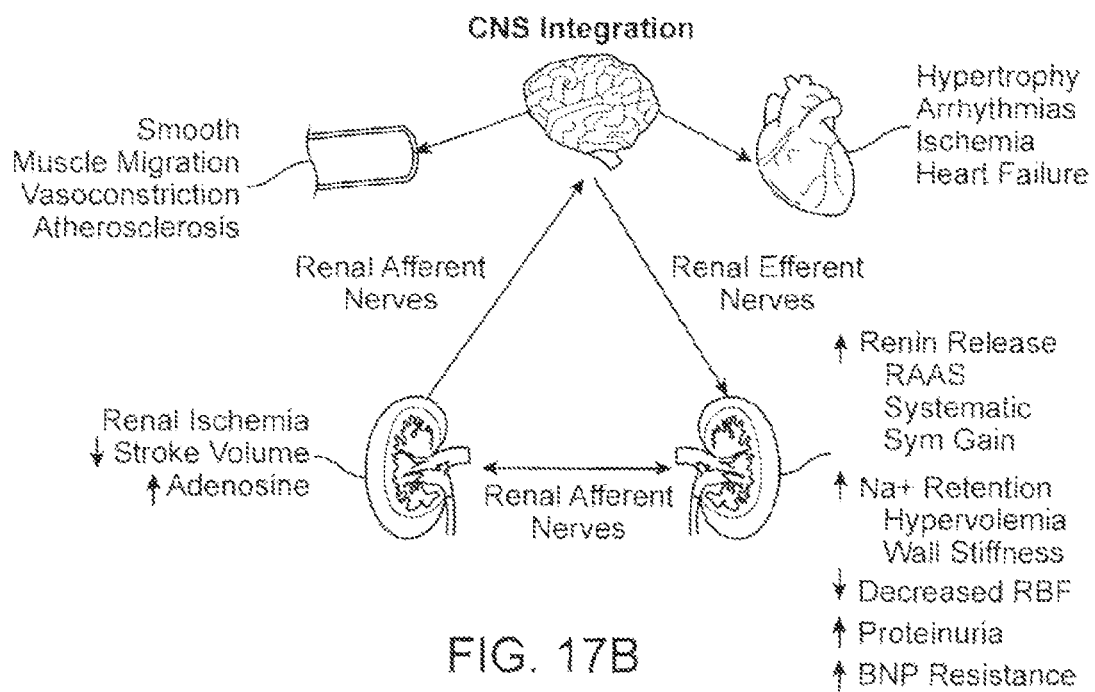

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 17A and 17B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal neuromodulation, a desirable reduction of central sympathetic outflow to various other sympathetically innervated organs such as the heart and the vasculature is anticipated.

B. Additional Clinical Benefits of Renal Neuromodulation

As provided above, renal neuromodulation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal neuromodulation might also be useful in treating other conditions associated with systemic sympathetic hyperactivity. Accordingly, renal neuromodulation may also benefit other organs and bodily structures innervated by sympathetic nerves. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal neuromodulation.

C. Achieving Intravascular Access to the Renal Artery

Figures 18A, 18B:
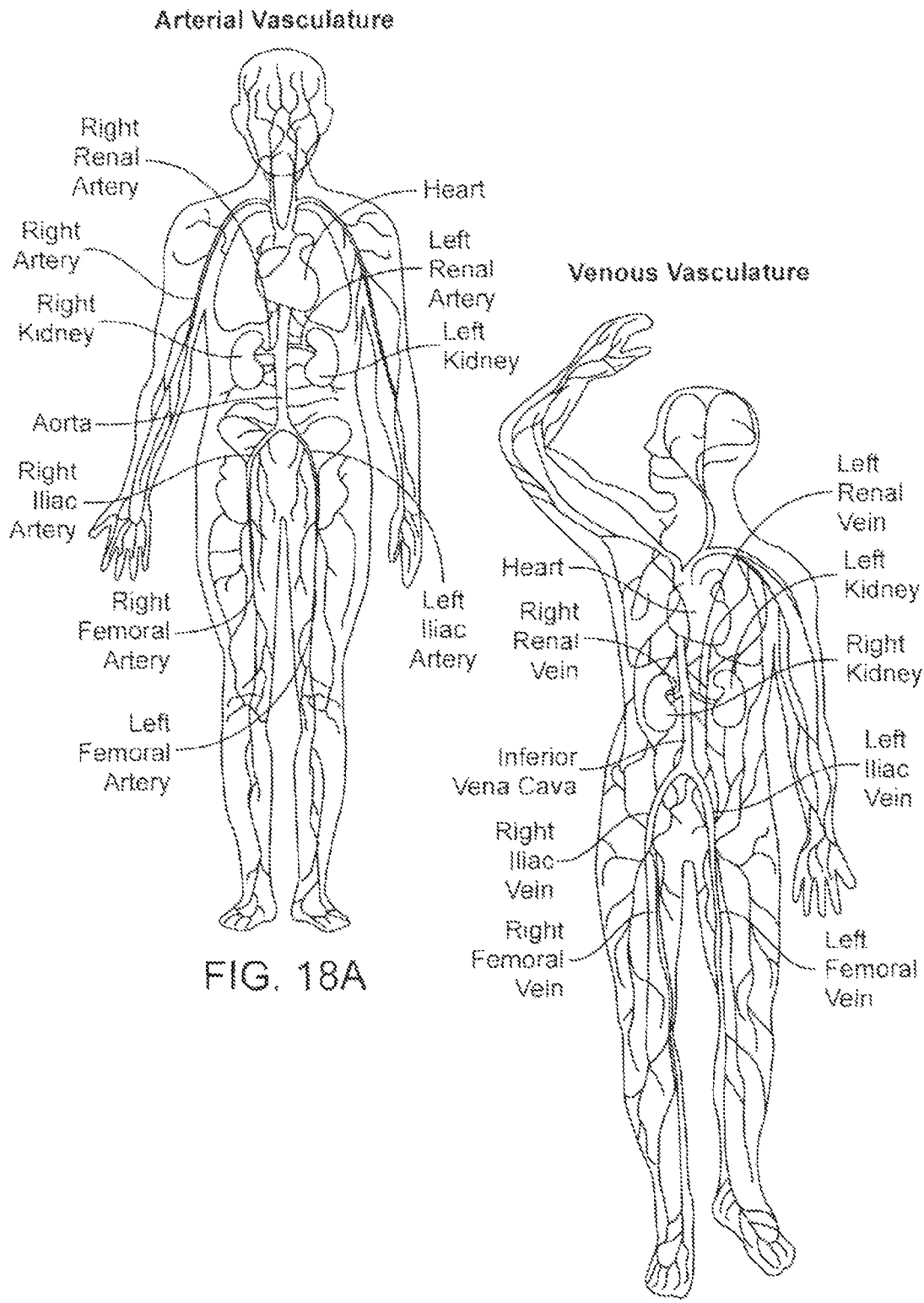
FIG. 18A shows human arterial vasculature.
FIG. 18B shows human venous vasculature.

In accordance with the present technology, neuromodulation of a left and/or right renal plexus (RP), which is intimately associated with a left and/or right renal artery, may be achieved through intravascular access. As FIG. 18A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 18B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or the right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, the brachial, or the axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or the right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, DRA, typically is in a range of about 2-10 mm, with most of the patient population having a DRA of about 4 mm to about 8 mm and an average of about 6 mm. Renal artery vessel length, LRA, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30 degrees-135 degrees.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for determining a position of an energy delivery element during intravascular neuromodulation, the method comprising:
    deploying an energy delivery element at a treatment site proximate a vessel wall;
    using a multi-region sensor at or adjacent to the energy delivery element to measure contact forces applied in a plurality of directions about the energy delivery element; and determining an orientation of the energy delivery element relative to the vessel wall based on the contact forces measured in the plurality of directions about the energy delivery element, wherein determining an orientation comprises:

measuring contact forces applied against a plurality of regions in the multi-region sensor, each region disposed to measure contact force impinging on the sensor at a different angle;

determining based on the measured contact forces which of a plurality of regions of the sensor is contacting the vessel wall; and determining an orientation of the energy delivery element based on the determination of which region of the sensor is contacting the vessel wall.

2. The method of claim 1, further comprising providing feedback to an operator to inform the operator when the multi-region sensor contacts the vessel wall based on measured contact forces.

3. The method of claim 1, further comprising providing feedback to an operator to inform the operator when the multi-region sensor contacts the vessel wall and to inform the operator of the orientation of the energy delivery element.

4. The method of claim 1, wherein measuring contact forces comprises using a capacitance of the plurality of regions to calculate contact force.

5. The method of claim 1, wherein the energy delivery element is an RF electrode, a thermal element, a cryo-ablation element, a microwave energy delivery element, an optical energy delivery element, or an ultrasonic transducer.

6. The method of claim 5, wherein the energy delivery element is an RF electrode.

7. The method of claim 6, wherein the vessel wall is a renal artery wall.

8. The method of claim 5, wherein the energy delivery element is a microwave energy delivery element.

9. The method of claim 5, wherein the energy delivery element is an ultrasonic transducer.

10. The method of claim 1, wherein the vessel wall is a renal artery wall.

11. A method for determining a position of an energy delivery element during intravascular neuromodulation, the method comprising:

deploying an energy delivery element at a treatment site proximate a vessel wall;

using a multi-region sensor at or adjacent to the energy delivery element to measure contact forces applied in a plurality of directions about the energy delivery element wherein the multi-region sensor comprises:

a first hollow conductive member;

a second hollow conductive member disposed coaxially within the first conductive member;

a plurality of non-conductive areas on the first conductive member, the non-conductive areas defining conductive regions about the first conductive member; and determining an orientation of the energy delivery element relative to the vessel wall based on the contact forces measured in the plurality of directions about the energy delivery element.

12. The method of claim 11, wherein the non-conductive areas comprise slots disposed in the second conductive annular ring.

13. A method for determining a position of an energy delivery element during intravascular neuromodulation, the method comprising:

deploying an energy delivery element at a treatment site proximate a vessel wall;

using a multi-region sensor at or adjacent to the energy delivery element to measure contact forces applied in a plurality of directions about the energy delivery element wherein the multi-region sensor comprises:

a first conductive annular ring; and a second conductive annular ring disposed coaxially within the first conductive annular ring and having a plurality of non-conductive areas defining conductive regions about the second conductive annular ring; and determining an orientation of the energy delivery element relative to the vessel wall based on the contact forces measured in the plurality of directions about the energy delivery element.

* * * * *